US005695995A

United States Patent [19]
Weintraub et al.

[11] Patent Number: 5,695,995
[45] Date of Patent: Dec. 9, 1997

[54] NEUROGENIC DIFFERENTIATION (NEUROD) GENES

[75] Inventors: Harold M. Weintraub, deceased, late of Seattle, Wash., by Nancy Weintraub, executrix; Jacqueline E. Lee, Denver, Colo.; Stanley M. Hollenberg, Portland, Oreg.; Stephen J. Tapscott, Seattle, Wash.

[73] Assignee: Fred Hutchinson Cancer Research Center, Seattle, Wash.

[21] Appl. No.: 552,142

[22] Filed: Nov. 2, 1995

Related U.S. Application Data

[63] Continuation-in-part of PCT/US95/05741, May 8, 1995, which is a continuation-in-part of Ser. No. 239,238, May 6, 1994, abandoned.

[51] Int. Cl.$^6$ ............... C12N 15/85; C12N 5/10; C12N 15/18
[52] U.S. Cl. ............ 435/325; 435/69.1; 435/69.4; 435/172.3; 435/252.33; 435/320.1; 435/357; 435/360; 536/23.1; 536/23.5; 536/23.51
[58] Field of Search ................ 435/69.1, 69.4, 435/172.3, 320.1, 240.2, 357, 325, 360, 252.33; 536/23.1, 23.5, 23.51

[56] References Cited

U.S. PATENT DOCUMENTS

| | | |
|---|---|---|
| 5,302,549 | 4/1994 | Blackwood et al. |
| 5,322,801 | 6/1994 | Kingston et al. |
| 5,352,595 | 10/1994 | Tapscott et al. |

OTHER PUBLICATIONS

Wilson, P.A. et al., "Induction of epidermis and inhibition of neural fate by Bmp-4," *Nature*, 376:331-333 (1995).

Lee, J.E. et al., "Conversion of *Xenopus* Ectoderm into Neurons by NeuroD, a basic Helix-Loop-Helix Protein," *Science*, 268:836-844 (1995).

Shimizu, C. et al., "MATH-2, a mammalian helix-loop-helix factor structurally related to the product of *Drosophila* proneural gene *atonal*, is specifically expressed in the nervous sysstem," *Eur. J. Biochem.*, 229:239-248 (1995).

Naya, F. J. et al., "Tissue-specific regulation of the insulin gene by a nove basic helix-loop-helix transcription factor," *Genes and Development*, 9:1009-1019 (1995).

Singson, A. et al., "Direct downstream targets of proneural activators in the imaginal disc include genes involved in lateral inhibitory signaling," *Genes & Development*, 8:2058-2071 (1994).

Turner, D.L. et al., "Expression of achaete-scute homolog 3 in *Xenopus* embryos converts ectodermal cells to a neural fate," *Genes & Development*, 8:1434-1447 (1994).

Rupp, R.A.W. et al., "*Xenopus* embryos regulate the nuclear localization of XMyoD," *Genes & Development*, 8:1311-1323 (1994).

Buffinger, N. et al., "Myogenic specification in somites: induction by axial structures," *Development*, 120:1443-1452 (1994).

Kramatschek, B. et al., "Neuroectodermal transcription of the *Drosophila* neurogenic genes E(spl) and HLH-m5 is regulated by proneural genes," *Development*, 120:815-826 (1994).

Burcin, M. et al., "Factors influencing nuclear receptors in transcriptional repression," *Cancer Biology*, 5:337-346 (1994).

Rudnicki, M.A., et al., "MyoD or Myf-5 Is Required for the Formation of Skeletal Muscle," *Cell*, 75:1351-1359 (1993).

Guillemot, F. et al., "Mammalian achaete-scute Homolog 1 is Required for the Early Development of Olfactory and Autonomic Neurons," *Cell*, 75:463-476 (1993).

Lamb, T.M. et al., "Neural Induction by the Secreted Polypeptide Noggin," *Science*, 262:713-718 (1993).

Hasty, P. et al., "Muscle deficiency and neonatal death in mice with a targeted mutation in the *myogenin* gene," *Nature*, 364:501-506 (1993).

Nabeshima, Y. et al., "*Myogenin* gene disruption results in perinatal lethality because of severe muscle defect," *Nature*, 364:532-535 (1993).

Guillemot, F. et al., "Dynamic expression of the murine Achaete-Scute homologue Mash-1 in the developing nervous system," *Mechanisms of Development*, 42:171-185 (1993).

Rong, P.M. et al., "The neural tube/notochord complex is necessary for vertebral but not limb and body wall striated muscle differentiation," *Development*, 115:657-672 (1992).

Lo, L.C. et al., "Mammalian achaete-scute homolog 1 is transiently expressed by spatially restricted subsets of early neuroepithelial and neural crest cells," *Genes & Development*, 5:1524-1537 (1991).

Blackwood, E.M. et al., "Max: A Helix-Loop-Helix Zipper Protein That Forms a Sequence-Specific DNA-Binding Complex with Myc," *Science*, 251:1211-1217 (1991).

Johnson, J.E. et al., "Two rat homologues of *Drosophila* achaete-scute specifically expressed in neuronal precursors," *Nature*, 346:858-861 (1990).

Maniatis et al., "Molecular cloning: a laboratory manual," Cold Spring Harbor Laboratory, Cold Spring Harbor, NY, 1982, p. 227.

Gen Bank NCBI gibbsq 109439, 1992, cited as MPSEARCH Result 11.

*Primary Examiner*—John L. LeGuyader
*Attorney, Agent, or Firm*—Christensen O'Connor Johnson & Kindness PLLC

[57] ABSTRACT

Neurogenic differentiation genes and proteins are identified, isolated, and sequenced. Expression of neuroD has been demonstrated in neural, pancreatic, and gastrointestinal cells. Ectopic expression of neuroD in non-neuronal cells of Xenopus embryos induced formation of neurons.

8 Claims, 1 Drawing Sheet

NeuroD: Mouse vs. Xenopus

MOUSE: NH₂ — [ E-rich | B | H1 | L | H2 | P-rich ] — COOH  355 aa / 39.8 kD

XENOPUS: NH₂ — [ D-rich | B | H1 | L | H2 | P-rich ] — COOH  352 aa / 39.6 kD

96% (50/52)

80% (159/198)

NEUROGENIC DIFFERENTIATION (NEUROD) GENES

This application is a continuation-in-part of international application No. PCT/US95/05741, filed May 8, 1995, which is a continuation-in-part of parent application U.S. Ser. No. 08/239,238, filed May 6, 1994 (abandoned).

This invention was made with government support under grant CA42506 awarded by the National Institutes of Health. The government has certain rights in the invention.

FIELD OF THE INVENTION

The invention relates to molecular biology and in particular to genes and proteins involved in vertebrate neural development.

BACKGROUND OF THE INVENTION

There are currently several examples of transcription regulatory proteins sharing a basic helix-loop-helix (bHLH) secondary structure. bHLH proteins form homodimeric and homodimeric complexes binding DNA in the 5' regulatory regions of genes controlling expression. Among the bHLH proteins, mammalian MyoD and Drosophila AS-C are presently thought to play developmental roles in muscle development and in sensory organ development, respectively. Both proteins are thought to exert their effects by binding 5' regulatory nucleotide sequences in genes that seem specifically determinative of cellular differentiation and fate. However, the specific developmental roles of the genes affected by MyoD and AS-C remain largely unknown, as are the molecular details of the developmental pathways regulated by these genes.

The presently disclosed NeuroD proteins represent a new sub-family of bHLH proteins and are implicated in vertebrate neuronal, endocrine and gastrointestinal development.

Subsequent to the filing of the parent application, Naya et al. (*Genes & Devel.* 9: 1009–1019, 1995) disclosed the isolation of a hamster bHLH transcription factor (BETA2) that binds to the insulin E-box sequence. Shimizu et al. (*Eur. J. Biochem.* 229: 239–248, 1995) disclosed the isolation of a mouse HLH protein, MATH-2 that is detected in neural tissue. Comparison of these sequences with the neuroD sequences disclosed herein demonstrate that they are members of the NeuroD family of proteins.

Neural tissues and endocrine tissues do not regenerate. Damage is permanent. Paralysis, loss of vision or hearing and hormonal insufficiency are also permanent. Tumors in neural and endocrine tissues can also be very difficult to treat because of the toxic side effects that conventional chemotherapeutic drugs may have on nervous tissues. The medical community and public would greatly benefit from the availability of agents active in triggering differentiation in neuroectodermal stem cells. Such neuronal differentiating agents could be used for construction of test cell lines, assays for identifying candidate therapeutic agents capable of inducing regeneration of neuronal and endocrine tissues, gene therapy, and differentiation of tumor cells.

SUMMARY OF THE INVENTION

Mammalian and amphibian NeuroD proteins were identified, and polynucleotide molecules encoding NeuroD proteins were isolated and sequenced. neuroD genes encode proteins that are distinctive members of the bHLH family. In addition, the present invention provides a family of NeuroD proteins that share a highly conserved HLH region. Representative polynucleotide molecules encoding members of the NeuroD family include neuroD, neuroD2 and neuroD3.

A representative nucleotide sequence encoding murine neuroD is shown in SEQ ID NO:1. The HLH coding domain of murine neuroD resides between nucleotides 577 and 696 in SEQ ID NO:1. The deduced amino acid sequence of murine NeuroD is shown in SEQ ID NO:2. There is a highly conserved region following the helix-2 domain from amino acid 150 through amino acid 199 of SEQ ID NO:2 that is not shared by other bHLH proteins.

A representative nucleotide sequence encoding Xenopus neuroD is shown in SEQ ID NO:3. The HLH coding domain of Xenopus neuroD resides between nucleotides 376 and 495 in SEQ ID NO:3. The deduced amino acid sequence of Xenopus NeuroD is shown in SEQ ID NO:4. There is a highly conserved region following the helix-2 domain from amine acid 157 through amine acid 199 of SEQ ID NO:4 that is not shared by other bHLH proteins.

Representative nucleotide and deduced amine acid sequences of the human NeuroD family are shown in SEQ ID NOS:8–15. Representative nucleotide and deduced amine acid sequences of a human homolog of murine neuroD are shown in SEQ ID NOS:8 and 9 (partial genomic sequence) and SEQ ID NOS:14 and 15 (human cDNA). Representative nucleotide and deduced amine acid sequences of the human and murine neuroD2 are shown in SEQ ID NOS:10 and 11, and 16 and 17, respectively. Representative nucleotide and deduced amine acid sequences for human neuroD3 are shown in SEQ ID NOS:12 and 13. The disclosed human clones, 9F1(and its corresponding cDNA HC2A; now referred to as human neuroD) and 14B1(now referred to as human neuroD2), have an identical HLH motif: amine acid residues 117–156 in SEQ ID NO:9 and 15, and residues 137–176 in SEQ ID NO:11 (corresponding to nucleotides 405–524 of SEQ ID NO:8 and SEQ ID NO:14, and nucleotides 463–582 of SEQ ID NO:10). Comparison of the deduced amine acid sequences of these neuroD genes shows that human NeuroD3 contains an HLH domain between amine acid residues 50–89 of SEQ ID NO:13 (corresponding to nucleotides 149–268 of SEQ ID NO:12) and that murine NeuroD2 contains an HLH domain between amine acids residues 138–177 of SEQ ID NO:17 (corresponding to nucleotides 642–761 of SEQ ID NO:16). The HLH domain of murine NeuroD2 is identical to the human NeuroD and human NeuroD2.

BRIEF DESCRIPTION OF THE DRAWINGS

FIG. 1 schematically depicts the domain structure of the murine and Xenopus NeuroD bHLH proteins.

DETAILED DESCRIPTION OF THE PREFERRED EMBODIMENTS

Tissue-specific bHLH proteins that regulate early neuroectodermal differentiation were discovered using expression cloning and screening assays designed to identify possible bHLH proteins capable of interacting with the protein product of the *Drosophila daughterless* gene. These proteins belong to a family of proteins that share conserved residues in the HLH region. The term NeuroD is generally used to encompass all members of the NeuroD family, and includes neuroD, neuroD2 and neuroD3 coding sequences and proteins.

NeuroD proteins are transiently expressed in differentiating neurons during embryogenesis. NeuroD is also detected in adult brain, in the granule layer of the hippocampus and the cerebellum. In addition, murine neuroD expression has been detected in the pancreas and gastrointestinal tissues of developing embryos and post-natal mice. NeuroD contains the basic helix-loop-helix (bHLH) domain structure that has been implicated in the binding of bHLH proteins to upstream recognition sequences and activation of downstream target genes. The present invention provides representative NeuroD proteins, which include the murine NeuroD protein of SEQ ID NO:2, the amphibian NeuroD protein of SEQ ID NO:4, murine NeuroD2 protein of SEQ ID NO:17, human NeuroD protein of SEQ ID NOS:9 and 15, human NeuroD2 protein of SEQ ID NO:11, and human NeuroD3 protein of SEQ D NO:13. Based on homology with other bHLH proteins, the bHLH domain for murine NeuroD is predicted to reside between amino acids 102 and 155 of SEQ ID NO:2, and between amino acids 101 and 157 of SEQ ID NO:4 for the amphibian NeuroD.

As detailed below, the present invention provides the identification of human neuroD and, in addition, provides unexpected homologous genes of the same family based on highly conserved sequences across the HLH domain shared between the two human genes at the amino acid level (neuroD2 and neuroD3; SEQ ID NOS:10 and 11, and 12 and 13, respectively).

NeuroD proteins are transcriptional activators that control transcription of downstream target genes that cause neuronal progenitors to differentiate into mature neurons. In the neurula stage of the mouse embryo (e10), murine neuroD is highly expressed in the neurogenic derivatives of neural crest cells, the cranial and dorsal root ganglia, and postmitotic cells in the central nervous system (CNS). During mouse development, neuroD is expressed transiently and concomitant with neuronal differentiation in differentiating neurons in sensory organs such as in nasal epithelium and retina. In Xenopus embryos ectopic expression of neuroD in non-neuronal cells induced formation of neurons. As discussed in more detail below, NeuroD proteins are expressed in differentiating neurons and are capable of causing the conversion of non-neuronal cells into neurons. The present invention encompasses NeuroD variants that, for example, are modified in a manner that results in a NeuroD protein capable of binding to its recognition site, but unable to activate downstream genes. The present invention also encompasses fragments of NeuroD that, for example, are capable of binding the natural NeuroD partner, but are incapable of activating downstream genes. NeuroD proteins encompass proteins retrieved from naturally occurring materials and closely related, functionally similar proteins retrieved by antisera specific to NeuroD, and recombinantly expressed proteins encoded by genetic materials (DNA, RNA, cDNA) retrieved on the basis of their similarity to the unique regions in the neuroD family of genes.

The present invention provides representative isolated and purified polynucleotide molecules encoding proteins of the NeuroD family. Representative polynucleotide molecules encoding NeuroD include the sequences presented in SEQ ID NOS:1, 3, 8, 10, 12, 14, and 16. Polynucleotide molecules encoding NeuroD include those sequences resulting in minor genetic polymorphisms, differences between species, and those that contain amino acid substitutions, additions, and/or deletions. According to the present invention, polynucleotide molecules encoding NeuroD encompass those molecules that encode NeuroD proteins or peptides that share identity with the sequences shown in SEQ ID NOS:2, 4, 9, 11, 13, 15, and 17. Such molecules will generally share greater than 35% identity at the amino acid level with the disclosed sequences. The polynucleotide molecules of the present invention may share greater identity at the amino acid level across highly conserved regions such as the HLH domain. For example, the deduced amino acid sequences of murine and Xenopus neuroD genes are 96% identical.

In some instances, one may employ such changes in the sequence of a recombinant neuroD to substantially decrease or even increase the biological activity of NeuroD relative to the wild-type NeuroD activity, depending on the intended use of the preparation. Such changes may also be directed towards endogenous neuroD sequences using, for example, gene therapy methods to alter the gene product.

The NeuroD proteins of the present invention are capable of inducing the expression of neuronal-specific genes, such as N-CAM, β-tubulin, and Xen-1, neurofilament M (NF-M), Xen-2, tanabin-1, shaker-1, and frog HSCL, in a frog embryo. As described below, NeuroD activity may be detected when NeuroD is ectopically expressed in frog oocytes following, for example, injection of Xenopus neuroD RNA into one of the two cells in a two-cell stage Xenopus embryo, and monitoring expression of neuronal-specific genes in the injected as compared to un-injected side of the embryo by immunochemistry or in situ hybridization.

"Over-expression" means an increased level of NeuroD protein or neuroD transcripts in a recombinant transformed host cell relative to the level of protein or transcripts in the parental cell from which the host cell is derived.

As noted above, the present invention provides isolated and purified polynucleotide molecules encoding NeuroD and other members of the NeuroD family. The disclosed sequences may be used to identify and isolate neuroD polynucleotide molecules from suitable host cells such as canine, ovine, bovine, caprine, lagomorph, or avian. In particular, the nucleotide sequences encoding the HLH region may be used to identify polynucleotide molecules encoding other proteins of the NeuroD family. Complementary DNA molecules encoding NeuroD family members may be obtained by constructing a cDNA library mRNA from, for example, fetal brain, newborn brain, adult brain and brain tissues. DNA molecules encoding NeuroD family members may be isolated from such a library using the disclosed sequences in standard hybridization techniques (e.g., Sambrook et al., ibid., and Bothwell, Yancopoulos and Alt, ibid.) or by amplification of sequences using polymerase chain reaction (PCR) amplification (e.g, Loh et al., *Science* 243: 217–222, 1989; Frohman et al., *Proc. Natl. Acad Sci. USA* 85: 8998–9002, 1988; and Erlich (ed.), *PCR Technology: Principles and Applications for DNA Amplification*, Stockton Press, 1989; which are incorporated by reference herein in their entirety). In a similar manner, genomic DNA encoding NeuroD may be obtained using probes designed from the sequences disclosed herein. Suitable probes for use in identifying neuroD sequences may be obtained from neuroD-specific sequences that are highly conserved regions between mammalian and amphibian neuroD coding sequences. Primers, for example, from the region encoding the approximately 40 residues following the helix-2 domain are suitable for use in designing PCR primers. Alternatively, oligonucleotides containing specific DNA sequences from a human neuroD coding region may be used within the described methods to identify related human neuroD genomic and cDNA clones. Upstream regulatory regions of neuroD may be obtained using the same methods. Suitable PCR primers are between 7–50 nucleotides in length, more preferably between 15 and 25 nucleotides in length. Alternatively, neuroD polynucleotide molecules may be isolated using standard hybridization techniques with probes of at least about 7 nucleotides in length and up to and including the full coding sequence. Southern analysis of mouse genomic DNA probed with the murine neuroD cDNA under stringent conditions showed the presence of only one gene, suggesting that under stringent conditions bHLH genes from other protein families will not be identified. Other members of the neuroD family can be identified using degenerate oligonucleotides based on the sequences disclosed herein for PCR amplification or by hybridization at moderate stringency.

The regulatory regions of neuroD may be useful as tissue-specific promoters. Such regulatory regions may find use in, for example, gene therapy to drive the tissue-specific expression of heterologous genes in pancreatic, gastrointestinal, or neural cells, tissues or cell lines. As shown in Example 14, murine neuroD promoter sequences reside within the 1.4 kb 5' untranslated region. Regulatory sequences within this region are identified by comparison to other promoter sequences and/or deletion analysis of the region itself.

A DNA molecule ceding a NeuroD protein is inserted into a suitable expression vector, which is in turn used to transfect or transform a suitable host cell. Suitable expression vectors for use in carrying out the present invention include a promoter capable of directing the transcription of a polynucleotide molecule of interest in a host cell. Representative expression vectors may include both plasmid and/or viral vector sequences. Suitable vectors include retroviral vectors, vaccinia viral vectors, CMV viral vectors, BLUE-SCRIPT™ vectors, baculovirus vectors, and the like. Promoters capable of directing the transcription of a cloned gene or cDNA may be inducible or constitutive promoters and include viral and cellular promoters. For expression in mammalian host cells, suitable viral promoters include the immediate early cytomegalovirus promoter (Boshart et al., *Cell* 41: 521–530, 1985) and the SV40 promoter (Subramani et al., *Mol. Cell. Biol.* 1: 854–864, 1981). Suitable cellular promoters for expression of proteins in mammalian host cells include the mouse metallothionien-1 promoter (Palmiter et al., U.S. Pat. No. 4,579,821), a mouse Vκ promoter (Bergman et al., *Proc. Natl. Acad Sci. USA* 81: 7041–7045, 1983; Grant et al. *Nucleic Acid Res.* 15: 5496, 1987), and tetracycline-responsive promoter (Gossen and Bujard, *Proc. Natl. Acad Sci. USA* 89: 5547–5551, 1992, and Pescini et al., *Biochem. Biophys. Res. Comm.* 202: 1664–1667, 1994). Also contained in the expression vectors, typically, is a transcription termination signal located downstream of the coding sequence of interest. Suitable transcription termination signals include the early or late polyadenylation signals from SV40 (Kaufman and Sharp, *Mol. Cell. Biol.* 2: 1304–1319, 1982), the polyadenylation signal from the Adenovirus 5 e1B region, and the human growth hormone gene terminator (DeNoto et al., *Nucleic Acid Res.* 9: 3719–3730, 1981). Mammalian cells, for example, may be transfected by a number of methods including calcium phosphate precipitation Wigler et al., *Cell* 14: 725, 1978; Corsaro and Pearson, *Somatic Cell Genetics* 7: 603, 1981; Graham and Van der Eb, *Virology* 52: 456, 1973), lipofection, microinjection, and electropotation (Neumann et al., *EMBO J.* 1: 8410845, 1982). Mammalian cells can be transduced with viruses such as SV40, CMV, and the like. In the case of viral vectors, cloned DNA molecules may be introduced by infection of susceptible cells with vital particles. Retroviral vectors may be preferred for use in expressing NeuroD proteins in mammalian cells particularly if NeuroD is used for gene therapy (for review, see, Miller et al. *Methods in Enzymology* 217: 581–599, 1994; which is incorporated herein by reference in its entirety). It may be preferable to use a selectable marker to identify cells that contain the cloned DNA. Selectable markers are generally introduced into the cells along with the cloned DNA molecules and include genes that confer resistance to drugs, such as neomycin, hygromycin, and methotrexate. Selectable markers may also complement auxotrophies in the host cell. Yet other selectable markers provide detectable signals, such as beta-galactosidase to identify cells containing the cloned DNA molecules. Selectable markers may be amplifiable. Such amplifiable selectable markers may be used to amplify the number of sequences integrated into the host genome.

As would be evident to one of ordinary skill in the art, the polynucleotide molecules of the present invention may be expressed in *Saccharomyces cerevisiae*, filamentous fungi, and *E coli*. Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990; and "Guide to Yeast Genetics and Molecular Biology," *Methods in Enzymology*, Guthrie and Fink (eds.), Academic Press, San Diego, Calif., 1991; which are incorporated herein by reference). Filamentous fungi may also be used to express the proteins of the present invention; for example, strains of the fungi Aspergillus (McKnight et al., U.S. Pat. No. 4,935,349, which is incorporated herein by reference). Methods for expressing genes and cDNAs in cultured mammalian cells and in *E coli* are discussed in detail in Sambrook et al. (*Molecular Cloning: A Laboratory Manual, Second Edition*, Cold Spring Harbor, N.Y., 1989; which is incorporated herein by reference). As will be evident to one skilled in the art, one can express the protein of the instant invention in other host cells such as avian, insect, and plant cells using regulatory sequences, vectors and methods well established in the literature.

NeuroD proteins produced according to the present invention may be purified using a number of established methods such as affinity chromatography using anti-NeuroD antibodies coupled to a solid support. Fusion proteins of antigenic tag and NeuroD can be purified using antibodies to the tag. Additional purification may be achieved using conventional purification means such as liquid chromatography, gradient centrifugation, and gel electrophoresis, among others. Methods of protein purification are known in the art (see generally, Scopes, R., *Protein Purification*, Springer-Verlag, N.Y., 1982, which is incorporated herein by reference) and may be applied to the purification of recombinant NeuroD described herein.

The term "capable of hybridizing under stringent conditions" as used herein means that the subject nucleic acid molecules (whether DNA or RNA) anneal to an oligonucleotide of 15 or more contiguous nucleotides of SEQ ID NO:1, SEQ ID NO:3, SEQ ID NO:8, SEQ ID NO:10, SEQ ID NO:12, SEQ ID NO:14 or SEQ ID NO:16.

The choice of hybridization conditions will be evident to one skilled in the art and will generally be guided by the purpose of the hybridization, the type of hybridization (DNA-DNA or DNA-RNA), and the level of desired relatedness between the sequences. Methods for hybridization are well established in the literature. See, for example: Sambrook et al., ibid.; Hames and Higgins, eds, *Nucleic Acid Hybridization, A Practical Approach*, IRL Press, Washington D.C., 1985; Berger and Kimmel, eds, *Methods in Enzymology, Vol. 52, Guide to Molecular Cloning Techniques*, Academic Press Inc., New York, N.Y., 1987; and Bothwell, Yancopoulos and Alt, eds, Methods for *Clon-* ing and Analysis of Eukaryotic Genes, Jones and Bartlett Publishers, Boston, Mass. 1990; which are incorporated by reference herein in their entirety. One of ordinary skill in the art realizes that the stability of nucleic acid duplexes will decrease with an increased number and location of mismatched bases; thus, the stringency of hybridization may be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/or the temperature. Stringency of hybridization may be reduced by reducing the percentage of formamide in the hybridization solution or by decreasing the temperature of the wash solution. High stringency conditions may involve high temperature hybridization (e.g., 65°–68° C. in aqueous solution containing 4–6× SSC, or 42° C. in 50% formamide) combined with high temperature (e.g., 5°–25° C. below the $T_m$) and a low salt concentration (e.g., 0.1× SSC). Reduced stringency conditions may involve lower hybridization temperatures (e.g., 35°–42° C. in 20–50% formamide) with intermediate temperature (e.g., 40°–60° C.) and washes in a higher salt concentration (e.g., 2–6× SSC). Moderate stringency conditions, which may involve hybridization at a temperature between 50° C. and 55° C. and washes in 0.1× SSC, 0.1% SDS at between 50° C. and 55° C., may be used to identify clones encoding members of the NeuroD family.

The invention provides isolated and purified polynucleotide molecules encoding NeuroD proteins that are capable of hybridizing under stringent conditions to an oligonucleotide of 15 or more contiguous nucleotides of SEQ ID NO:1, SEQ ID NO:3, SEQ ID NO:8, SEQ ID NO:10, SEQ ID NO:12, SEQ ID NO:14, and/or SEQ ID NO:16, including theft complementary strands. The subject isolated neuroD polynucleotide molecules preferably encode NeuroD proteins that trigger differentiation in ectodermal cells, particularly neuroectodermal stem cells, and in more committed cells of that lineage, for example, epidermal precursor cells, pancreatic and gastrointestinal cells. Such neuroD expression products typically form heterodimeric bHLH protein complexes that bind in the 5'-regulatory regions of target genes and enhance or suppress transcription of the target gene.

In some instances, cancer cells may contain a non-functional NeuroD protein or may contain no NeuroD protein due to genetic mutation or somatic mutations such that these cells fail to differentiate. For cancers of this type, the cancer cells may be treated in a manner to cause the over-expression of wild-type NeuroD protein to force differentiation of the cancer cells.

Antisense neuroD nucleotide sequences may be used to block expression of mutant neuroD expression in neuronal precursor cells to generate and harvest neuronal stem cells. The use of antisense oligonucleotides and their applications have been reviewed in the literature (see, for example, Mol and Van der Krul, eds., *Antisense Nucleic Acids and Proteins Fundamentals and Applications*, New York, N.Y., 1992; which is incorporated by reference herein in its entirety). Suitable antisense oligonucleotides are at least 11 nucleotide in length and may include untranslated (upstream or intron) and associated coding sequences. As will be evident to one skilled in the art, the optimal length of an anti sense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structure in the mRNA and/or in the antisense oligonucleotide. Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression. A particularly preferred target region for antisense oligonucleotide is the 5' untranslated (promoter/enhancer) region of the gene of interest. Antisense oligonucleotides may be prepared by the insertion of a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense oligonucleotides. Alternatively, antisense oligonucleotides may be synthesized using standard manual or automated synthesis techniques. Synthesized oligonucleotides may be introduced into suitable cells by a variety of means including electroporation, calcium phosphate precipitation, or microinjection. The selection of a suitable antisense oligonucleotide administration method will be evident to one skilled in the art. With respect to synthesized oligonucleotides, the stability of antisense oligonucleotide-mRNA hybrids may be increased by the addition of stabilizing agents to the oligonucleotide. Stabilizing agents include intercalating agents that are covalently attached to either or both ends of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates, or phosphorodithioates. Oligonucleotides may also be made nuclease resistant by synthesis of the oligonucleotides with alpha-anomers of the deoxyribonucleotides.

NeuroD binds to 5' regulatory regions of neurogenic genes that are involved in neuroectodermal differentiation, including development of neural and endocrine tissues. As described in more detail herein, murine neuroD has been detected in neuronal, pancreatic and gastrointestinal tissues in embryonic and adult mice suggesting that NeuroD functions in the transcription regulation in these tissues. NeuroD proteins alter the expression of subject genes by, for example, down-regulating or up-regulating transcription, or by inducing a change in transcription to an alternative open reading frame. The subject polynucleotide molecules find a variety of uses, e.g., in preparing oligonucleotide probes, expression vectors, and transformed host cells, as disclosed below in the following Examples.

DNA sequences recognized by NeuroD may be determined using a number of methods known in the literature including immunoprecipitation (Biedenkapp et al, *Nature* 335: 835–837, 1988; Kinzler and Vorgelstein, *Nuc. Acids Res.* 17: 3645–3653, 1989; and Sompayrac and Danna, *Proc. Natl. Acad Sci. USA* 87: 3274–3278, 1990; which are incorporated by reference herein), protein affinity columns (Oliphant et at., *Mol. Cell. Biol.* 9: 2944–2949, 1989; which is incorporated by reference herein), gel mobility shifts (Blackwell and Weintraub, *Science* 250: 1104–1110, 1990; which is incorporated by reference herein), and Southwestern blots (Keller and Maniatis, *Nuc. Acids Res.* 17:4675–4680, 1991; which is incorporated by reference herein).

One embodiment of the present invention involves the construction of interspecies hybrid NeuroD proteins and hybrid NeuroD proteins containing one or more domains from another NeuroD family member to facilitate structure-function analyses or to alter NeuroD activity by increasing or decreasing the transcriptional activation of neurogenic genes by NeuroD relative to the wild-type NeuroD(s). Hybrid proteins of the present invention may contain the replacement of one or more contiguous amino acids of the native NeuroD with the analogous amino acid(s) of NeuroD from another species or other protein of the NeuroD family. Such interspecies or interfamily hybrid proteins include hybrids having whole or partial domain replacements. Such hybrid proteins are obtained using recombinant DNA techniques. Briefly, DNA molecules encoding the hybrid NeuroD proteins of interest are prepared using generally available methods such as PCR mutagenesis, site-directed mutagenesis, and/or restriction digestion and ligation. The hybrid DNA is then inserted into expression vectors and introduced into suitable host cells. The biological activity may be assessed essentially as described in the assays set forth in more detail in the Examples that follow.

The invention also provides synthetic peptides, recombinantly derived peptides, fusion proteins, and the like that include a portion of NeuroD or the entire protein. The subject peptides have an amino acid sequence encoded by a nucleic acid which hybridizes under stringent conditions with an oligonucleotide of 15 or more contiguous nucleotides of SEQ ID NO:1, SEQ ID NO:3, SEQ ID NO:8, SEQ ID NO:10, SEQ ID NO:12, SEQ ID NO:14, or SEQ ID NO:16. Representative amino acid sequences of the subject peptides are disclosed in SEQ ID NO:2, SEQ ID NO:4, SEQ ID NO:9, SEQ ID NO:11, SEQ ID NO:13, SEQ ID NO:15, and SEQ ID NO:17. The subject peptides find a variety of uses, including preparation of specific antibodies and preparation of antagonists of NeuroD activity.

As noted above, the invention provides antibodies that bind to NeuroD. The production of non-human antisera or monoclonal antibodies (e.g., murine, lagomorph, porcine, equine) is well known and may be accomplished by, for example, immunizing an animal with NeuroD protein or peptides. For the production of monoclonal antibodies, antibody producing cells are obtained from immunized animals, immortalized and screened, or screened first for the production of the antibody that binds to the NeuroD protein or peptides and then immortalized. It may be desirable to transfer the antigen binding regions (e.g., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397; which is incorporated by reference herein in its entirety. Alternatively, a human monoclonal antibody or portions thereof may be identified by first screening a human B-cell cDNA library for DNA molecules that encode antibodies that specifically bind to NeuroD, e.g., according to the method generally set forth by Huse et al. (*Science* 246: 1275-1281, 1989, which is incorporated by reference herein in its entirety). The DNA molecule may then be cloned and amplified to obtain sequences that encode the antibody (or binding domain) of the desired specificity.

The invention also provides methods for inducing the expression of genes associated with neuronal phenotype in a cell that does not normally express those genes. Examples of neuronal phenotypes that may be modulated by NeuroD expression include expression of neurotransmitters or neuromodulatory factors. Cells that can be used for the purpose of modulation of gene expression by NeuroD include cells of the neuroectodermal lineage, glial cells, neural crest cells, and epidermal epithelial basal stem cells, and all types of both mesodermal and endodermal lineage cells. NeuroD expression may also be used within methods that induce expression of genes associated with pancreatic and gastrointestinal phenotype. Examples of such gene expression include insulin expression, and gastrointestinal-specific enzyme expression.

As illustrated in Example 10, the expression of Xenopus NeuroD protein in stem cells causes redirection of epidermal cell differentiation and induces terminal differentiation into neurons, i.e., instead of epidermal cells. Epithelial basal stem cells (i.e., in skin and mucosal tissues) are one of the few continuously regenerating cell types in an adult mammal. Introduction of the subject nucleotide sequences into an epithelial basal stem cell may be accomplished in vitro or in vivo using a suitable gene therapy vector delivery system (e.g., a retroviral vector), a microinjection technique (see, for example, Tam, *Basic Life Sciences* 37: 187-194, 1986, which is incorporated by reference herein in its entirety), or a transfection method (e.g., naked or liposome encapsulated DNA or RNA; see, for example, *Trends in Genetics* 5: 138, 1989; Chen and Okayama, *Biotechniques* 6: 632-638, 1988; Mannino and Gould-Fogerite, *Biotechniques* 6: 682-690, 1988; Kojima et al., *Biochem. Biophys. Res. Comm.* 207: 8-12, 1995; which are incorporated by reference herein in their entirety). The introduction method may be chosen to achieve a transient expression of NeuroD in the host cell, or it may be preferable to achieve constitutive or regulated expression in a tissue specific manner.

Transformed host cells of the present invention find a variety of in vitro uses, for example: i) as convenient sources of neuronal and other growth factors, ii) in transient and continuous cultures for screening anti-cancer drugs capable of driving terminal differentiation in neural tumors, iii) as sources of recombinantly expressed NeuroD protein for use as an antigen in preparing monoclonal and polyclonal antibodies useful in diagnostic assays, and iv) in transient and continuous cultures for screening for compounds capable of increasing or decreasing the activity of NeuroD.

Transformed host cells of the present invention also find a variety of in vivo uses, for example, for transplantation at sites of traumatic neural injury where motor or sensory neural activity has been lost. Representative patient populations that may benefit from transplantation include: patients with hearing or vision loss due to optical or auditory nerve damage, patients with peripheral nerve damage and loss of motor or sensory neural activity, and patients with brain or spinal cord damage from traumatic injury. For example, donor cells from a patient such as epithelial basal stem cells are cultured in vitro and then transformed or transduced with a neuroD nucleotide sequence. The transformed cells are then returned to the patient by microinjection at the site of neural dysfunction. In addition, transformed host cells of the present invention may be useful for transplantation into patients with diabetes. For example, donor cells from a patient such as fibroblasts, pancreatic islet cells, or other pancreatic cells are harvested and transformed or transfected with a neuroD nucleotide sequence. The genetically engineered cells are then returned to the patient. In another embodiment, such engineered host cells may find use in the treatment of malabsorption syndromes.

Representative uses of the nucleotide sequences of the invention include the following:

1. Construction of cDNA and oligonucleotide probes useful in Northern, Southern, and dot-blot assays for identifying and quantifying the level of expression of neuroD in a cell. High level expression of neuroD in neuroendocrine tumors and in rapidly proliferating regions of embryonic neural development (see below) indicates that measuring the level of neuroD expression may provide prognostic markers for assessing the growth rate and invasiveness of a neural tumor. In addition, considering the important role of NeuroD in embryonic development it is thought highly likely that birth defects and abortions may result from expression of an abnormal NeuroD protein. In this case, NeuroD may prove highly useful in prenatal screening of mothers and/or for in utero testing of fetuses.

2. Construction of recombinant cell lines, ova, and transgenic embryos and animals including dominant-negative and "knock-out" recombinant cell lines in which the transcription regulatory activity of NeuroD protein is down-regulated or eliminated. Such cells may contain altered neuroD coding sequences that result in the expression of a NeuroD protein that is not capable of enhancing, suppressing or activating transcription of the target gene. The subject cell lines and animals find uses in screening for candidate therapeutic agents capable of either substituting for a function performed by NeuroD or correcting the cellular defect caused by a defective NeuroD. Considering the important regulatory role of NeuroD in embryonic development, birth defects may occur from expression of mutant NeuroD proteins, and these defects may be correctable in utero or in early post-natal life through the use of compounds identified in screening assays using NeuroD. In addition, neuroD polynucleotide molecules may be joined to reporter genes, such as β-galactosidase or luciferase, and inserted into the genome of a suitable embryonic host cell such as a mouse embryonic stem cell by, for example, homologous recombination (for review, see Capecchi, *Trends in Genetics* 5: 70–76, 1989; which is incorporated by reference). Cells expressing NeuroD may then be obtained by subjecting the differentiating embryonic cells to cell sorting, leading to the purification of a population of neuroblasts. Neuroblasts may be useful for studying neuroblast sensitivity to growth factors or chemotherapeutic agents. The neuroblasts may also be used as a source from which to purify specific protein products or gene transcripts. These products may be used for the isolation of growth factors, or for the identification of cell surface markers that can be used to purify stem cell population from a donor for transplantation.

As illustrated in Example 14, "knock-out" mice were generated by replacing the murine neuroD coding region with the β-galactosidase reporter gene and the neomycin resistance gene to assess the consequences of eliminating the murine NeuroD protein and to examine the tissue distribution of NeuroD in fetal and postnatal mice. Mice that were homozygous for the mutation (lacking NeuroD) had diabetes, as demonstrated by high blood glucose levels, and died by day four. Homozygous mutants had blood glucose levels between 2 and 3 times the blood glucose level of wild-type mice. Heterozygous mutants exhibited similar blood glucose levels as wild-type mice. Examination of stained tissue from fetal and postnatal mice heterozygous for the mutation confirmed the NeuroD expression pattern in neuronal cells demonstrated by in situ hybridization (Example 4) and also demonstrated neuroD expression in the pancreas and gastrointestinal tract.

"Knock-out" mice may be useful as a model system for diabetes. Such mice may be used to study methods to rescue homozygous mutants and as hosts to test transplant tissue for treating diabetes.

3. Construction of gene transfer vectors (e.g., retroviral vectors, and the like) wherein neuroD is inserted into the coding region of the vector under the control of a promoter. neuroD gene therapy may be used to correct traumatic neural injury that has resulted in loss of motor or sensory neural function, and also for the treatment of diabetes. For these therapies, gene transfer vectors may either be injected directly at the site of the traumatic injury, or the vectors may be used to construct transformed host cells that are then injected at the site of the traumatic injury. The results disclosed in Example 10 indicate that introduction of neuroD induces a non-neuronal cell to become a neuron. This discovery raises for the first time the possibility of using transplantation and/or gene therapy to repair neural defects resulting from traumatic injury. In addition, the discovery of neuroD provides the possibility of providing specific gene therapy for the treatment of certain neurological disorders such as Alzheimer's disease, Huntington's disease, and Parkinson's disease, in which a population of neurons have been damaged. Two basic methods of neuroD utilization are envisioned in this regard. In one method, neuroD is expressed in existing populations of neurons to modulate aspects of their neuronal phenotype (e.g., neurotransmitter expression or synapse targeting) to make the neurons express a factor or phenotype to overcome the deficiency that contributes to the disease. In this method, recombinant neuroD sequences are introduced into existing neurons or endogenous neuroD expression is induced. In another method, neuroD is expressed in non-neuronal cells (e.g., glial cells in the brain or another non-neuronal cell type such as basal epithelial cells) to induce expression of genes that confer a complete or partial neuronal phenotype that ameliorates aspects of the disease. As an example, Parkinson's disease is caused, at least in part, by the death of neurons that supply the neurotransmitter dopamine to the basal ganglia. Increasing the levels of neurotransmitter ameliorates the symptoms of Parkinson's disease. Expression of neuroD in basal ganglia neurons or glial cells may induce aspects of a neuronal phenotype such that the neurotransmitter dopamine is produced directly in these cells. It may also be possible to express neuroD in donor cells for transplantation into the affected region, either as syngeneic or allogeneic transplantations. Within yet another embodiment, neuroD is expressed in non-pancreatic cells to induce expression of genes that confer a complete or partial pancreatic phenotype that ameliorates aspects of diabetes. Within yet another embodiment, neuroD is expressed in pancreatic islet cells to induce expression of genes that induce the expression of insulin.

4. Preparation of transplantable recombinant neuronal precursor cell populations from embryonic ectodermal cells, non-neural basal stem cells, and the like. Establishing cultures of non-malignant neuronal cells for use in therapeutic screening assays has proven to be a difficult task. The isolated polynucleotide molecules encoding NeuroD of the present invention permit the establishment of primary (or continuous) cultures of proliferating embryonic neuronal stem cells under conditions mimicking those that are active in development and cancer. The resultant cell lines find uses: i) as sources of novel neural growth factors, ii) in screening assays for anti-cancer compounds, and iii) in assays for identifying novel neuronal growth factors. High level expression of neuroD in the embryonic optic rectum (see below) indicates that NeuroD protein may regulate expression of factors trophic for growing retinal cells. Such cells may be useful sources of growth factors, and may be useful in screening assays for candidate therapeutic compounds.

The cell lines and transcription regulatory factors disclosed herein offer the unique advantage that since they are active very early in embryonic differentiation they represent potential switches, e.g., ON→OFF or OFF→ON, controlling subsequent cell fate. If the switch can be shown to be reversible (i.e., ON↔OFF), the NeuroD transcription regulatory factor and neuroD nucleic acids disclosed herein provide exciting opportunities for restoring lost neural and/or endocrine functions in a subject.

The following examples are offered by way of illustration and not by way of limitation.

EXAMPLE 1

Construction of the embryonic stem cell "179" cDNA libray

A continuous murine embryonic stem cell line (i.e., the ES cell line) having mutant E2A (the putative binding partner of myoD) was used as a cell source to develop a panel of embryonic stem cell tumors. Recombinant ES stem cells were constructed (i.e., using homologous recombination) wherein both alleles of the putative myoD binding partner E2A were replaced with drug-selectable marker genes. ES cells do not make functional E12 or E47 proteins, both of which are E2A gene products. ES cells form subcutaneous tumors in congenic mice (i.e., 129J) that appear to contain representatives of many different embryonal cell types as judged histologically and through the use of RT-PCR gene expression assays. Individual embryonic stem cell tumors were induced in male 129J strain mice by subcutaneous injection of $1 \times 10^7$ cells/site. Three weeks later each tumor was harvested and used to prepare an individual sample of RNAs. Following random priming and second strand synthesis the ds-cDNAs were selected based on their size on 0.7% agarose gels and those cDNAs in the range of 400–800 bp were ligated to either Bam HI or Bgl II linkers. (Linkers were used to minimize the possibility that an internal Bam HI site in a cDNA might inadvertently be cut during cloning, leading to an abnormally sized or out-of-frame expression product.) The resultant individual stem cell tumor DNAs were individually ligated into the Bam HI cloning site in the "fl-VP16" 2μ yeast expression vector. This expression vector, fl-VP16, contains the VP16 activation domain of Herpes simplex virus (HSV) located between Hind III (HIII) and Eco RI (RI) sites and under the control of the *Saccharomyces cereviseae* alcohol dehydrogenase promoter; with LEU2 and Ampicillin-resistance selectable markers. Insertion of a DNA molecule of interest into the Hind HI site of the fl-VP 16 vector (i.e., 5' to the VP16 nucleotide sequence), or into a Bam HI site (i.e., 3' to the VP16 sequence but 5' to the Eco RI site), results in expression of a VP16 fusion protein having the protein of interest joined in-frame with VP 16. The resultant cDNA library was termed the "179-library".

EXAMPLE 2

Identification and cDNA cloning of neuroD

A two-hybrid yeast screening assay was used essentially as described by Fields and Song (Nature 340: 245, 1989) and modified as described herein was used to screen the 179-library described in Example 1. Yeast two-hybrid screens are reviewed as disclosed in Fields and Sternglanz (*Trends in Genetics* 10: 286–292, 1994). The library was screened for cDNAs that interacted with LexA-Da, a fusion protein between the Drosophila Da (Daughterless) bHLH domain and the prokaryotic LexA-DNA binding domain. Multimerized LexA binding sites were cloned upstream of two reporter genes, the HIS3 gene and the β-galactosidase gene. The *S. cereviseae* strain L40 containing a plasmid encoding the LexA-Da fusion protein was transformed with CsCl gradient-purified fl-VP16-179-cDNA library. Transformants were maintained on medium selecting both plasmids (the LexA-Da plasmid and the cDNA library plasmid) for 16 hours before being subjected to histidine selection on plates lacking histidine, leucine, tryptophan, uracil, and lysine. Clones that were HIS$^+$ were subsequently assayed for the expression of LacZ. To eliminate possible non-specific cloning artifacts, plasmids from HIS$^+$/LacZ$^+$ were isolated and transformed into *S. cereviseae* strain L40 containing a plasmid encoding a LexA-Lamin fusion. Clones that scored positive in the interaction with lamin were discarded. Approximately 400 cDNA clones, which represented 60 different transcripts, were identified as positive in these assays. Twenty-five percent of the original clones were subsequently shown to be known bHLH genes on the basis of their reactivity with specific cDNA probes. One cDNA clone encoding a VP16-fusion protein that interacted with Da but not lamin was identified as unique by sequence analysis. This clone, initially termed tango, is now referred to as neuroD.

The unique cDNA identified above, VP 16-neuroD, contained an approximately 450 bp insert that spanned the bHLH region. Sequence analysis showed that the clone contained an insert encoding a complete bHLH amino acid sequence motif that was unique and previously unreported. Further analysis suggested that while the cDNA contained conserved residues common to all members of the bHLH protein family, several residues were unique and made it distinct from previously identified bHLH proteins. The neuroD cDNA insert was subcloned as a Bam HI-Not I insert into Bam HI-Not I linearized pBluescript SK$^+$. The resulting plasmid was designated pSK+1-83.

The neuroD insert contained in the VP16-neuroD plasmid was used to re-probe a mouse cDNA library prepared from mouse embryos at developmental stage e10.5. Candidate clones were isolated and sequenced essentially as described above. Several clones were isolated. One clone, designated pKS$^+$m7a RX, was deposited at the American Type Culture Collection, 12301 Parklawn Drive, Rockville, Md. 20852 USA, on May 6, 1994, under accession number 75768. Plasmid pKS m7a RX contains 1646 bp of murine neuroD cDNA as an EcoRI-XhoI insert. The amino acid sequence encoded by the insert begins at amino acid residue +73 and extends to the carboxy-terminus of the NeuroD protein. The plasmid contains about 855 bp of NeuroD coding sequence. (encoding amino acids 73–536).

None of the mouse cDNAs contained the complete 5' coding sequence. To obtain the 5' neuroD coding sequence, a mouse strain 129/Sv genomic DNA library was screened with the VP16-neuroD plasmid insert (450 bp). Genomic clones were isolated and sequenced and the sequences were aligned with the cDNA sequences. Alignment of the sequence and comparison of the genomic 5' coding sequences with the Xenopus neuroD clone (Example 8) confirmed the 5' neuroD coding sequence. The complete neuroD coding sequence and deduced amino acid sequence are shown in SEQ ID NOS: 1 and 2.

EXAMPLE 3

NeuroD/neuroD bHLH proteins share common structural similarities that include a basic region that binds DNA and an HLH region involved in protein-protein interactions required for the formation of homodimers and heterodimeric complexes. A comparison of the amino acid sequence of the basic region of murine NeuroD (amino acids 102 to 113 of SEQ ID NO:2) with basic regions of other bHLH proteins revealed that murine NeuroD contained all of the conserved residues characteristic among this family of proteins. However, in addition, NeuroD contained several unique residues. These unique amino acid residues were not found in any other known HLH making NeuroD a distinctive new member of the bHLH family. The NARERNR basic region motif in NeuroD (amino acids 107–113 of SEQ ID NO:2) is also found in the Drosophila AS-C protein, a protein thought to be involved in neurogenesis. Similar, but not identical, NARERRR and NERERNR motifs (SEQ ID NOS:5 and 6, respectively) have been found in the Drosophila Atonal and MASH (mammalian achaete-scute homolog) proteins, respectively, which are also thought to be involved in neurogenesis. The NARER motif (SEQ ID NO:7) of neuroD is shared by other bHLH proteins, and the Drosophila Daughterless (Da) and Mammalian E proteins. The basic region of bHLH proteins is important for DNA binding site recognition, and there is homology between NeuroD and other neuro-proteins in this functional region. Within the important dimer-determining HLH region of NeuroD, a low level of homology was recorded with mouse twist protein (i.e., 51% homology) and with MASH (i.e., 46% homology). NeuroD contains several regions of unique peptide sequence within the bHLH domain including the junction sequence (MHG).

EXAMPLE 4

NeuroD is expressed in differentiating neurons during embryonic development neuroD expression was analyzed during embryonic development of mouse embryos using in situ hybridization with an antisense neuroD single-stranded riboprobe labeled with digoxigenin (Boehringer Mannheim). Briefly, a riboprobe was prepared from plasmid pSK+1-83 using T7 polymerase and digoxigenin-11-UTP for labeling. The hybridized probe was detected using anti-digoxigenin antibody conjugated with alkaline phosphatase. Color development was carried out according to the manufacturer's instruction. Stages of development are commonly expressed as days following copulation and where formation of the vaginal plug is e0.5. The results recorded in the in situ hybridization studies were as follows:

In the e9.5 mouse embryo, neuroD expression was observed in the developing trigerminal ganglia.

In the e10.5 mouse embryo, a distinctive pattern of neuroD expression was observed in all the cranial ganglia (i.e., V–XI) and in dorsal root ganglia (DRG) in the trunk region of the embryo. At this time neuroD expression was also observed in the central nervous system in post-mitotic cells in the brain and spinal cord that were undergoing neuronal differentiation. In the spinal cord, the ventral portion of the cord from which the motor neurons arise and differentiate was observed to express neuroD at high levels; and expression in the posterior-ventral spinal cord was higher when compared to more mature anterior-ventral spinal cord.

In the e11.5 mouse embryo, the ganglionic expression pattern of neuroD observed in e10.5 persisted. Expression in the spinal cord was increased over the level of expression observed in e10.5 embryos, which is consistent with the presence of more differentiating neurons at this stage. At this stage neuroD expression is also observed in other sensory organs in which neuronal differentiation occurs, for example, in the nasal epithelium, otic vesicle, and retina of the eye. In both of these organs neuroD expression was observed in the region containing differentiating neurons.

In the e14.5 mouse embryo, expression of neuroD was observed in cranial ganglia and DRG, but expression of neuroD persisted in the neuronal regions of developing sensory organs and the central nervous system (CNS). Thus, neuroD expression was observed to be transient during neuronal development.

In summary, expression of neuroD in the neurula stage of the embryo (e10), in the neurogenic derivatives of neural crest cells, the cranial and dorsal root ganglia, and post mitotic cells in the CNS suggests an important possible link between expression and generation of sensory and motor nerves. Expression occurring later in embryonic development in differentiating neurons in the CNS and in sensory organs (i.e., nasal epithelium and retina) also supports a role in development of the CNS and sensory nervous tissue. Since neuroD expression is transient, the results suggest that neuroD expression is operative as a switch controlling formation of sensory nervous tissue. It is noteworthy that in these studies neuroD expression was not observed in embryonic sympathetic and enteric ganglia (also derived from migrating neural crest cells). Overall, the results indicate that neuroD plays an important role in neuronal differentiation.

EXAMPLE 5

NeuroD is expressed in neural and brain tumor cells: murine probes identify human neuroD Given the expression pattern in mouse embryo (Example 4), Northern blots of tumor cell line mRNAs were examined using murine neuroD cDNA (Example 2) as a molecular probe. As a first step, cell lines that have the potential for developing into neurons were screened. The D283 human medullablastoma cell line, which expressed many neuronal markers, expressed high levels of neuroD by Northern blot analysis. neuroD was also transcribed at various levels by different human neuroblastoma cell lines and in certain rhabdomyosarcoma lines that are capable of converting to neurons. Murine PC12 pheochromacytoma cells and P19 embryocarcinoma cells differentiate into neurons in tissue culture in the presence of appropriate inducers, i.e., nerve growth factor and retinoic acid, respectively. When induced, murine P19 but not PC12 cells expressed neuroD transcripts. However, non-induced murine PC12 cells, P19 cells, and control 3T3 fibroblasts did not produce detectable levels of neuroD transcripts. Thus, PC12 and P19 cells represent cell types that are potentially useful in screening assays for identifying inducers of neuroD expression that may stimulate nerve regeneration and differentiation of neural tumor cells.

EXAMPLE 6

Recombinant cells expressing NeuroD

Recombinant murine 3T3 fibroblast cells expressing either a myc-tagged murine NeuroD protein or myc-tagged Xenopus NeuroD protein were made. The recombinant cells were used as a test system for identifying antibody to NeuroD described below.

Xenopus NeuroD protein was tagged with the antigenic marker Myc to allow the determination of the specificity of anti-NeuroD antibodies to be determined. Plasmid CS2+MT was used to produce the Myc fusion protein. The CS2+MT vector (Turner and Weintraub, ibid.) contains the simian cytomegalovirus IE94 enhance/promoter (and an SP6 promoter in the 5' untranslated region of the IE94-driven transcript to allow in vitro RNA synthesis) operatively linked to a DNA sequence encoding six copies of the Myc epitope tag (Roth et al, *J. Cell Biol.* 115: 587–596, 1991; which is incorporated herein in its entirety), a polylinker for insertion of coding sequences, and an SV40 late polyadenylation site. CS2-MT was digested with Xho I to linearize the plasmid at the polylinker site downstream of the DNA sequence encoding the myc tag. The linearized plasmid was blunt-ended using Klenow and dNTPs. A full length Xenopus cDNA clone was digested with Xho I and Eae I and blunt-ended using Klenow and dNTPs, and the 1.245 kb fragment of the Xenopus neuroD cDNA was isolated. The neuroD fragment and the linearized vector were ligated to form plasmid CS2+MT x1-83.

CS2+MT was digested with Eco RI to linearize the plasmid at the polylinker site downstream of the DNA sequence encoding the myc tag. The linearized plasmid was blunt-ended using Klenow and dNTPs and digested with Xho I to obtain a linearized plasmid having an Xho I adhesive end and a blunt end. Plasmid pKS+m7a containing a partial murine neuroD cDNA was digested with Xho I, and the NeuroD containing fragment was blunt-ended and digested with Xba I to obtain the approximately 1.6 kb fragment of the murine neuroD cDNA. The neuroD fragment and the linearized vector were ligated to form plasmid CS2+MT M1–83(m7a).

Plasmids CS2+MT x1-83 and CS2+MT M1-83(m7a) were each transformed into murine 3T3 fibroblast cells and used as a test system for identifying antibody against NeuroD (Example 7).

EXAMPLE 7

Antibodies to NeuroD

A recombinant fusion protein of maltose binding protein (MBP) and amine acid residues 70–355 of murine NeuroD was used as an antigen to evoke antibodies in rabbits. Specificity of the resultant antisera was confirmed by immunostaining of the recombinant 3T3 cells described above. Double-immunostaining of the recombinant cells was observed with monoclonal antibodies to Myc (i.e., the control antigenic tag on the transfected DNA) and with rabbit anti-murine NeuroD in combination with anti-rabbit IgG. The specificity of the resultant anti-murine NeuroD sera was investigated further by preparing mouse 3T3 fibroblasts cells transfected with different portions of NeuroD DNA. Specificity seemed to map to the glutamic acid-rich domain (i.e., amine acids 66–73 of SEQ ID NO:2). The anti-murine antisera did not react with cells transfected with the myc-tagged Xenopus neuroD. In a similar manner, Xenopus NeuroD was used to generate rabbit anti-NeuroD antisera. The antisera was Xenopus-specific and did not cross react with cells transfected with myc-tagged murine neuroD.

EXAMPLE 8

NeuroD is a highly evolutionarily conserved protein: sequence of Xenopus NeuroD Approximately one million clones from a stage 17 Xenopus head library made by Kintner and Melton (Development 99: 311, 1987) were screened with the mouse cDNA insert as a probe at low stringency. The hybridization was performed with 50% formamide/4× SSC at 33° C. and washed with 2× SSC/0.1% SDS at 40° C.

Positive clones were identified and sequenced. Analysis of the Xenopus neuroD cDNA sequence (SEQ ID NO:3) revealed that NeuroD is a highly conserved protein between frog and mouse. The deduced amino acid sequences of frog and mouse (SEQ ID NOS:2 and 4) show 96% identity in the bHLH domain (50 of 52 amino acids are identical) and 80% identity in the region that is carboxy-terminal to the bHLH domain (159 of 198 amino acids are identical). The domain structures of murine and Xenopus NeuroD are highly homologous with an "acidic" N-terminal domain (i.e., glutamic or aspartic acid rich); a basic region; helix 1, loop, helix 2; and a proline rich C-terminal region. Although the amino terminal regions of murine and Xenopus NeuroD differ in amino acid sequence, both retain a glutamic or aspartic acid rich "acidic domain" (amino acids 102 to 113 of SEQ ID NO:2 and amino acids 56 to 79 of SEQ ID NO:4). It is highly likely that the acidic domain constitutes an "activation" domain for the NeuroD protein, in a manner analogous to the activation mechanisms currently understood for other known transcription regulatory factors.

EXAMPLE 9

Neuronal expression of Xenopus neuroD

The expression pattern of neuroD in whole mount Xenopus embryos was determined using in situ hybridization with a single stranded digoxigenin-labeled Xenopus neuroD antisense cDNA riboprobe. Embryos were examined at several different stages.

Consistent with the mouse expression pattern, by late stage, all cranial ganglia showed very strong staining patterns. In Xenopus, as in other vertebrate organisms, neural crest cells give rise to skeletal components of the head, all ganglia of the peripheral nervous system, and pigment cells. Among these derivatives, the cranial sensory ganglia, which are of mixed crest and placode origin, represent the only group of cells that express neuroD. High levels of neuroD expression in the eye were also observed, correlating with active neuronal differentiation in the retina at this stage. Expression is observed in the developing olfactory placodes and otic vesicles, as was seen in mice. The pineal gland also expressed neuroD. All of this expression in transient, suggesting that neuroD functions during the differentiation process but is not required for maintenance of these differentiated cell types.

As early as stage 14 (i.e., the mid-neurula stage) neuroD expression was observed in the cranial neural crest region where trigerminal ganglia differentiate. Primary mechanosensory neurons in the spinal cord, also referred to as Rohon-Beard cells and primary motor neurons, showed neuroD expression at this stage.

By stage 24, all of the developing cranial ganglia, trigerminal, facio-acoustic, glosso-pharyngeal, and vagal nervous tissues showed a high level of neuroD expression. High levels of expression of neuroD was also observed in the eye at this stage. (Note that in Xenopus neuronal differentiation in the retina occurs at a much earlier stage than in mice, and neuroD expression was correspondingly earlier and stronger in this animal model.)

In summary, in Xenopus as in mouse, neuroD expression was correlated with sites of neuronal differentiation. The remarkable evolutionary conservation of the pattern of neuroD expression in differentiating neurons supports the notion that NeuroD has been evolutionarily conserved both structurally and functionally in these distant classes, which underscores the critical role performed by this protein in embryonic development.

EXAMPLE 10

Ectopic expression of neuroD converts non-neuronal cells into neurons

To further analyze the biological functions of NeuroD, a gain-of-function assay was conducted. In this assay, RNA was microinjected into one of the two cells in a 2-cell stage Xenopus embryo, and the effects on later development of neuronal phenotype was evaluated. For these experiments myc-tagged neuroD transcripts were synthesized in vitro using SP6 RNA polymerase. The myc tagged-neuroD transcripts were microinjected into one of the two cells in a Xenopus 2-cell embryo, and the other cell of the embryo served as an internal control. Antibodies to Xenopus N-CAM, a neural adhesion molecule, anti-Myc (to detect the exogenous protein), and immunostaining techniques were used to evaluate phenotypic expression of the neuronal marker (and control) gene during the subsequent developmental stages of the microinjected embryos. Remarkably, an evaluation of over 130 embryos that were injected with neuroD RNA showed a striking increase in ectopic expression of N-CAM on the microinjected side of the embryo (i.e., Myc$^+$), as judged by increased immunostaining. The increased staining was observed in the region from which neural crest cells normally migrate. It is considered likely that ectopic expression (or over-expression) of neuroD caused neural crest stem cells to follow a neurogenic cell fate. Outside the neural tube, the ectopic immunostaining was observed in the facio-cranial region and epidermal layer, and in some cases the stained cells were in the ventral region of the embryo far from the neural tube. The immunostained cells not only expressed N-CAM ectopically, but displayed a morphological phenotype of neuronal cells. At high magnification, the N-CAM expressing cells exhibited typical neuronal processes reminiscent of axonal processes.

To confirm that the ectopic N-CAM expression resulted from a direct effect on the presumptive epidermal cells and not from aberrant neural cell migration into the lateral and ventral epidermis, neuroD RNA was injected into the top tier of 32-cell stage embryos, in order to target the injection into cells destined to become epidermis. N-CAM gaining was observed in the lateral and ventral epidermis without any noticeable effect on the endogenous nervous system, indicating that the staining of N-CAM in the epidermis represents the conversion of epidermal cell fate into neuronal cell fate.

Ectopic generation of neurons by neuroD was confirmed with other neural specific markers, such as neural-specific class II β-tubulin (Richter et at., *Proc. Natl. Acad. Sci. USA* 85: 8066, 1988), acetylated alpha-tubulin (Piperno and Fuller, *J. Cell. Biol.* 101: 2085, 1985), tanabin (Hemmati-Brinvanlou et at., *Neuron* 9: 417, 1992), neurofilament (NF)-M (Szaro et at., *J. Comp. Neurol.* 273: 344, 1988), and Xen-1,2 (Ruiz i Altaba, *Development* 115: 67, 1992). The embryos were subjected to immunochemistry as described by Turner and Weintraub (*Genes Dev.* 8:1434, 1994, which is incorporated by reference herein) using primary antibodies detected with alkaline phosphatase-conjugated goat anti-mouse or anti-rabbit antibodies diluted to 1:2000 (Boehringer-Mannheim). Anti-acetylated alpha-tubulin was diluted 1:2000. Anti-Xen-1 was diluted 1:1. Anti-NF-M was diluted 1:2000. Embryos stained for NF-M were fixed in Dent's fixative (20% dimethylsulfoxide/80% methanol) and cleared in 2:1 benzyl benzoate/benzyl alcohol as described by Dent et at. (*Development* 105: 61, 1989, which is incorporated by reference herein). In situ hybridization of embryos was carried out essentially as described by Harland (in *Methods in Cell Biology*, B. K. Kay, H. J. Pend, Eds, Academic Press, New York, N.Y., Vol 36, pp. 675–685, 1991, which is incorporated by reference herein) as modified by Turner and Weintraub (ibid.). In situ hybridization with β-tubulin without RNase treatment can also detect tubulin expression in the ciliated epidermal cells. All of these markers displayed ectopic sting on the neuroD RNA injected side. Injection of neuroD mRNA into vegetal cells led to no ectopic expression of neural markers except in one embryo that showed internal N-CAM staining in the trunk region, suggesting the absence of cofactors or the presence of inhibitors in vegetal cells. However, the one embryo that showed ectopic neurons in the internal organ tissue suggests that it may be possible to convert non-ectodermal lineage cells into neurons under certain conditions.

The embryos were also stained with markers that detect Rohon-Beard cells (cells in which neuroD is normally expressed). Immunostaining using the method described above for Rohon-Beard cell-specific markers such as HNK-1 (Nordlander, *Dev. Brain Res.* 50: 147, 1989, which is incorporated by reference herein) at a dilution of 1:1, Islet-1 (Ericson et al., *Science* 256: 1555, 1992 and Korzh et al., *Development* 118: 417, 1993) at a dilution of 1:500, and in situ hybridization as described above with shaker-1 (Ribera et al., *J. Neurosci.* 13: 4988, 1993) showed more cells staining on the injected side of the embryos.

The combined results support the notion that ectopic expression of NeuroD induced differentiation of neuronal cells from cells that, without neuroD microinjection, would have given rise to non-neuronal cells. In summary, these experiments support the notion that ectopic neuroD expression can be used to convert a non-neuronal cell (i.e., uncommitted neural crest cells and epidermal epithelial basal stem cells) into a neuron. These findings offer for the first time the potential for gene therapy to induce neuron formation in injured neural tissues.

Interesting morphological abnormalities were observed in the microinjected embryos. In many cases the eye on the microinjected side of the embryo failed to develop. In other embryos, the spinal cord on the microinjected side of the embryo failed to develop properly, and the tissues were strongly immunopositive when stained with anti-N-CAM. In addition, at the mid-neurula stage many microinjected embryos exhibited an increase in cell mass in the cranial region of the embryo from which (in a normal embryo) the neural crest cells and their derivatives (i.e., cranial ganglionic cells) would migrate. The observed cranial bulge exhibited strong immunostaining with antibodies specific for N-CAM. These results were interpreted to mean that morphological changes in the eye, neural crest, and spinal cord resulted from premature neural differentiation which altered the migration of neural and neural crest precursor cells.

NeuroD-injected embryos were also assayed for alteration in the expression of Xtwist, the Xenopus homolog of Drosophila twist, to determine whether neuroD converted non-neuronal components of neural crest cells into the neural lineage. In wild-type embryos, Xtwist is strongly expressed in the non-neuronal population cephalic neural crest cells that give rise to the connective tissue and skeleton of the head. neuroD-injected embryos were completely missing Xtwist expression in the migrating cranial neural crest cells on the injected side. The failure to generate sufficient cranial mesenchymal neural crest precursors in neuroD-injected embryos was also observed morphologically, since many of the injected embryos exhibited poor branchial arch development in the head. Furthermore, the increased mass of cells in the cephalic region stained very strongly for N-CAM, β-tubulin, and Xen-1, indicating that these cells were neural in character.

The converse experiment in which frog embryos were injected with Xtwist mRNA showed that ectopic expression of Xtwist significantly decreased neuroD expression on the injected side. Thus, two members of the bHLH family, neuroD and Xtwist, may compete for defining the identity of different cell types derived from the neural crest. In the neuroD-injected embryos, exogenous neuroD may induce premigratory neural crest to differentiate into neurons in situ, and consequently they fail to migrate to their normal positions.

The effect of introduction of exogenous neuroD on the fate of cells that normally express neuroD, such as cranial ganglia, eye, otic vesicle, olfactory organs, and primary neurons, and on other CNS cells that normally do not express neuroD, was determined by staining for differentiation markers. When the cranial region of the embryo is severely affected by ectopic neuroD, the injected side of the embryos displayed either small or no eyes in addition to poorly organized brains, otic vesicles, and olfactory organs. Moreover, as the embryos grew, the spinal cord showed retarded growth, remaining thinner and shorter on the neuroD-injected side.

N-CAM staining in the normal embryo at early stages was not uniform throughout the entire neural plate, but rather was more prominent in the medial region of the neural plate. Injected embryos analyzed for N-CAM expression show that the neural plate on the injected side of the early stage embryos was stained more intensely and more laterally. The increase in N-CAM staining was not associated with any lateral expansion of the neural plate as assayed by visual inspection and staining with the epidermal marker EpA. This was in contrast to what has been observed with XASH-3 injection that causes neural plate expansion. These observations suggest that the first effects of neuroD are to cause neuronal precursors in the neural plate to differentiate prematurely.

To determine whether neuroD caused neuronal precursors to differentiate prematurely, injected embryos were stained using two neuronal markers that are expressed in differentiated neurons, neural specific β-tubulin and tanabin. In situ hybridization for β-tubulin and tanabin was carried out as described above. Over-expression of neuroD dramatically increased the β-tubulin signals in the region of the neural plate containing both motor neurons and Rohon-Beard cells at stage 14. The earliest ectopic β-tubulin positive cells on the injected side were observed at the end of gastrulation when the control side did not yet show any β-tubulin positive cells. Tanabin was also expressed in more cells in the spinal cord in the neuroD injected side of the embryos at stage 14. These results suggest that neuroD can cause premature differentiation of the neural precursors into differentiated neurons. This is a powerful indication that, when ectopically expressed or over-expressed, NeuroD can differentiate mitotic cells into non-dividing mature neurons.

EXAMPLE 11

Human genomic clones of neuroD, neuroD2 and neuroD3

Genomic clones encoding human NeuroD were obtained by probing a human fibroblast genomic library with the mouse neuroD cDNA. Host *E coli* strain LE392 (New England Biolabs) were grown in LB+10 mM $MgSO_4$ 0.2% maltose overnight at 37° C. The cells were harvested and resuspended in 10 mM $MgSO_4$ to a final OD600 of 2. The resuspended cells were used as hosts for phage infection. The optimal volume of phage stock for use in this screening was determined by using serial dilutions of the phage stock of a human fibroblast genomic library in lambda FIX II (Stratagene) to infect LE392 cells (New England Biolabs). To obtain approximately 50,000 plaques per plate, a 2.5 µl aliquot of the phage stock was used to infect 600 µl of the resuspended LE392 cells. The cells were incubated with the phage for 15 minutes at 37° C, after which the cells were mixed with 6.5 ml of top agar warmed to 50° C. The top agar was plated on solid LB, and incubated overnight at 37° C. A total of 22 15-cm plates were prepared in this manner.

Duplicate plaque lifts were prepared. A first set of Hybond membranes (Amersham) were placed onto the plates and allowed to sit for 2 minutes. The initial membranes were removed and the duplicate membranes were laid on the plates for 4 minutes. The membranes were allowed to air dry; then the phage were denatured in 0.5M NaOH, 1.5M NaCl for 7 minutes. The membranes were neutralized with two washes in neutralization buffer (1.5M NaCl, 0.5M Tris, pH 7.2). Alter neutralization, the membranes were crosslinked by exposure to UV. A 1 kb Eco RI-Hind III fragment containing murine neuroD coding sequences was random primed using the Random Priming Kit (Boehringer Mannheim) according to the manufacturer's instructions. Membranes were prepared for hybridization by placing six membranes in 10 ml of FBI hybridization buffer [100 g polyethylene glycol 800, 350 ml 20% SDS, 75 ml 20× SSPE; add water to a final volume of one liter] and incubating the membranes at 65° C. for 10 minutes. After 10 minutes, denatured salmon sperm DNA was added to a final concentration of 10 µg/ml and denatured probe was added to a final concentration of $0.25-0.5 \times 10^7$ cpm/ml. The membranes were hybridized at 65° C. for a period of 8 hours to overnight. After incubation, the SDS for 30 minutes at 50° C. The first wash was followed by a final wash in 0.1× SSC, 0.1% SDS for 30 minutes at 55° C. Autoradiographs of the membranes were prepared. The first screen identified 55 putative positive plaques. Thirty-one of the plaques were subjected to a secondary screen using the method essentially set forth above. Ten positive clones were identified and subjected to a tertiary screen as described above. Eight positive clones were identified after the tertiary screen. Of these eight clones, three (14B1, 9F1 and 20A1) were chosen for further analysis. Clones 14B1 and 20A1 were deposited at the American Type Culture Collection, 1: 2301 Parklawn Drive, Rockville, Md. 20852 USA, on Nov. 1, 1995, under accession numbers 69943 and 69942, respectively.

Phage DNA was prepared from clones 14B1, 9F1, and 20A1. The 14B1 and 20A1 phage DNA were digested with Pst I to isolate the 1.2 kb and 1.5 kb fragments, respectively, that hybridized to the mouse neuroD probe. The 9F1 phage DNA was digested with Eco RI and SacI to obtain an approximately 2.2 kb fragment that hybridizes with the mouse neuroD probe. The fragments were each subcloned into plasmid BLUESCRIPT SK (Stratagene) that had been linearized with the appropriate restriction enzyme(s). The fragments were sequenced using Sequenase Version 2.0 (US Biochemical) and the following primers: the universal primer M13-21, the T7 primer, and the T3 primer. Sequence analysis of clones 9F1 (SEQ ID NOS:8 and 9), and 14B 1 (SEQ ID NOS:10 and 11) showed a high similarity between the mouse and human coding sequences at both the amino acid and nucleotide level. In addition, while clones 9F1 and 14B1 shared 100% identity in the HLH region at the amino acid level (i.e., residues 117–156 in SEQ ID NO:9 and residues 137–176 in SEQ ID NO:11), they diverged in the amino-terminal of the bHLH. This finding strongly suggests that 14B1 is a member of the neuroD family of genes. Sequence analysis demonstrates that clone 9F1 has a high degree of homology throughout the sequence region that spans the translation start site to the end of the bHLH region. The 9F1 clone has 100% identity to mouse NeuroD in the HLH region (i.e., residues 117–156 in SEQ ID NO:9 and residues 117–156 in SEQ ID NO:2), and an overall identity of 94%. The 14B1 clone also has 100% identity to the HLH region (i.e., residues 137–176 in SEQ ID NO:11 and residues 117–156 in SEQ ID NO:2), but only 40% identity to 9F1 and 39% identity to mouse NeuroD in the amino-terminal region. This demonstrates that 9F1 is the human homolog of mouse neuroD, whereas the strong conservation of the NeuroD HLH identifies 14B1 as another member of the neuroD HLH subfamily. Human clone 9F1 (represented by SEQ ID NOS:8 and 9) is referred to as human neuroD. Human clone 14B 1 is referred to as neuroD2 (SEQ ID NOS:10 and 11, and human clone 20A1 is referred to as neuroD3 (SEQ ID NOS:12 and 13).

An 800 bp Hind III-Eag I fragment from the neuroD2 sequences from clone 14B1 was random primed with $^{32}P$. This probe was used to screen a 16-day mouse embryo cDNA library essentially as described previously. Filters were prehybridized in FBI hybridization buffer (see above) at 50° C. for 10 minutes. After prehybridization, denatured salmon sperm DNA was added to a final concentration of 10 µg/ml; denatured probe was added to a final concentration of one million cpm/ml. The filter was hybridized at 50° C. overnight. After incubation, excess probe was removed, and the filter was washed first in 2× SSC, 0.1% SDS for 30 minutes at 60° C. One clone, designated 1.1.1, contained 1.46 kb of murine neuroD2 cDNA as an Eco RI-Hind IIII insert. The nucleotide sequence and deduced amino acid sequences are shown in SEQ ID NOS:16 and 17, respectively. A comparison between the human genomic sequence and the mouse cDNA sequence demonstrate that there were no introns in the human neuroD2 coding region.

In a similar manner, a random-primed 1.1 kb Pst I fragment from the human neuroD3 cDNA present in the 20A1 clone is prepared. The probe is used to screen a mouse embryo and newborn mouse brain libraries. Hybridization and wash conditions are as described above. Positive clones are analyzed by restriction and sequence analysis, and a full length clone is obtained. The mouse neuroD3 cDNA is used to prepare a probe for Northern analysis to study expression patterns in embryonic through adult mice.

Using a random-primed antisense probe to the mouse neuroD2 (Boehringer Mannheim) the expression pattern was determined using Northern analysis. Filters containing murine RNA from the brain and spinal cords of embryonic through adult mice were probed at high stringency and washed in 0.1× SSC, 0.1% SDS at 65° C. Northern analysis showed neuroD2 expression in the brain and spinal cords of mice from embryonic day 12.5 through adult.

EXAMPLE 12

Chromosome mapping of human neuroD clones

FISH karyotyping was performed on fixed metaphase spreads of the microcell hybrids essentially as described (Trask et al., *Am. J. Hum. Genet.* 48: 1–15, 1991; and Brandriff et al., *Genomics* 10: 75–82, 1991; which are incorporated by reference herein in their entirety). neuroD sequences were detected using the 9F1 or 20A1 phage DNA as probes labeled using digoxigenin dUTP (Boehringer Mannheim) according to the manufacturer's instructions. Phage DNA was biotinylated by random priming (Gibco/BRL BioNick Kit) and hybridized in situ to denatured metaphase chromosome spreads for 24–48 hours. Probes were detected with rhodamine-conjugated antibodies to digoxigenin, and chromosomes were counterstained with DAPI (Sigma). Signals were viewed through a fluorescence microscope and photographs were taken with color slide film. FISH analysis indicated clone 9F1 maps to human chromosome 2q, and clone 20A1 maps to human chromosome 5.

Chromosome mapping was also carried out on a human/rodent somatic cell hybrid panel (National Institute of General Medical Sciences, Camden, N.J.). This panel consists of DNA isolated from 24 human/rodent somatic cell hybrids retaining one human chromosome. For one set of experiments, the panel of DNA's were digested with Eco RI and electrophoresed on an agarose gel. The DNA was transferred to Hybond-N membranes (Amersham). A random primed (Boehringer Mannheim) 4 kb Eco RI-Sac I fragment of clone 9F1 was prepared. The filter was prehybridized in 10 ml of FBI hybridization buffer (see above) at 65° C. for 10 minutes. After prehybridization, denatured salmon sperm DNA was added to a final concentration of 10 µg/ml; denatured probe was added to a final concentration of one million cpm/ml. The filter was hybridized at 65° C. for a period of 8 hours to overnight. After incubation, excess probe was removed, and the filter was washed first in 2× SSC, 0.1% SDS for 30 minutes at 65° C. The first wash was followed by a final wash in 0.1× SSC, 0.1% SDS for 30 minutes at 65° C. An autoradiograph of the filter was prepared. Autoradiographs confirmed the FISH mapping results.

In the second experiment, the panel was digested with Pst I, electrophoresed and transferred essentially as described above. A random-primed (Boehringer Mannheim) 1.6 kb Psi I fragment of clone 20A1 was prepared. The membrane was prehybridized, hybridized with the 20A1 probe and washed as described above. Autoradiographs of the Southern showed that 20A1 mapped to human chromosome 5 and confirmed the FISH mapping results. After autoradiography, the 20A1-probed membrane was stripped by a wash in 0.5M NaOH, 1.5M NaCl. The membrane was neutralized in 0.5M Tris-HCl (pH 7.4), 1.5M NaCl. The filter was washed in 0.1× SSC before prehybridization. A random-primed (Boehringer Mannheim) 1.2 kb Pst I fragment of clone 14B1 was prepared. The washed membrane was prehybridized and hybridized with the 14B1 probe as described above. After washing under the previously described conditions, the membrane was autoradiographed. Autoradiographs demonstrated that clone 14B1 mapped to chromosome 17.

EXAMPLE 13

Human neuroD complementary DNA

To obtain a human neuroD cDNA, one million plaque forming units (pfu) were plated onto twenty LB+10 mM MgSO$_4$ (150 mm) plates using the Stratagene human cDNA library in Lambda ZAP II in the bacterial strain XL-1 Blue (Stratagene). Plating and membrane lifts were performed using standard methods, as described in Example 11. After UV cross-linking, the membranes were pre-hybridized in an aqueous hybridization solution (1% bovine serum albumin, 1 mM EDTA, 0.5M Na$_2$HPO$_4$ (pH 7.4), 7% SDS) at 50° C. for two hours.

The mouse neuroD cDNA insert was prepared by digesting the pKS+m7a RX plasmid with Eco RI and Xho I, and isolating the fragment containing the cDNA by electroelution. A probe was made with the cDNA containing fragment by random primed synthesis with random hexanucleotides, dGTP, dATP, dTTP, alpha-$^{32}$P-labeled dCTP, and Klenow in a buffered solution (25 mM Tris (pH6.9), 50 mM KCl, 5 mM $MgCl_2$, 1 mM DTT). The probe was purified from the unincorporated nucleotides on a G-50 sepharose column. The purified probe was heat denatured at 90° C. for 3 minutes.

After prehybridization, the denatured probe was added to the membranes in hybridization solution. The membranes were hybridized for 24 hours at 50° C. Excess probe was removed from the membranes, and the membranes were washed in 0.1× SSC, 0.1% SDS for 20 minutes at 50° C. The wash solution was changed five times. The membranes were blotted dry and covered with plastic film before being subjected to autoradiography. Autoradiography of the filters identified 68 positive clones. The clones are plaque-purified and rescreened to obtain 40 pure, positive clones. The positive clones were screened with a random-primed Pst I fragment from clone 9F1 (human neuroD). Twelve positive clones that hybridized with the human neuroD genomic probe were isolated.

The plasmid vector containing cDNA insert was excised in vivo from the lambda phage clone according to the Stratagene methodology. Briefly, eluted phage and XL-1 Blue cells (200 microliters of OD 600=1) were mixed with R408 helper phage provided by Stratagene for 15 minutes at 37° C. Five milliliters of rich bacterial growth media (2 X YT, see Sambrook et at., ibid.) was added, and the cultures were incubated for 3 hours at 37° C. The tubes were heated at 70° C. for 20 minutes and spun for 5 minutes at 4,000×g. After centrifugation, 200 microliters of supernatant was added to the same volume of XL-1 Blue cells (OD=1), and the mixture was incubated for 15 minutes at 37° C, after which the bacterial cells were plated onto LB plates containing 50 µg/ml ampicillin. Each colony was picked and grown for sequencing template preparation. The clones were sequenced and compared to the human genomic sequence. A full length cDNA encoding human neuroD that was identical to the 9F1 neuroD genomic sequence was obtained and designated HC2A. The nucleotide and deduced amino acid sequences are shown in SEQ ID NOS:14 and 15, respectively. Clone HC2A was deposited at the American Type Culture Collection, 12301 Parklawn Drive, Rockville, Md. 20852 USA, on Nov. 1, 1995, under accession number 69944.

EXAMPLE 14

Construction of knock-out mice

Knock-out mice in which the murine neuroD coding sequence was replaced with the β-galactosidase gene and the neomycin resistance gene (neo) were generated i) to assess the consequences of eliminating the murine NeuroD protein during mouse development and ii) to permit examination of the expression pattern of neuroD in embryonic mice. Genomic neuroD sequences used for these knock-out mice were obtained from the 129/Sv mice so that the homologous recombination could take place in a congenic background in 129/Sv mouse embryonic stem cells. Several murine neuroD genomic clones were isolated from a genomic library prepared from 129/Sv mice (Zhuang et at., Cell 79: 875–884, 1994; which is incorporated herein by reference in its entirety) using the Bam HI-Not I neuroD cDNA containing fragment of pSK+1-83 (Example 2) as a random-primed probe essentially as described in Example 11. Plasmid pPNT (Tybulewicz et at., Cell 65: 1153–1163, 1991; which is incorporated herein by reference in its entirety) containing the neomycin resistance gene (neo; a positive selection marker) and the Herpes simplex virus thymidine kinase gene (hsv-tk, a negative selection marker) under the control of the PGK promoter provided the vector backbone for the targeting construct. A 1.4 kb 5' murine neuroD genomic fragment together with the 3 kb cytoplasmic β-galactosidase gene were inserted between the Eco RI and Xba I sites of the pPNT vector, and an 8 kb fragment containing the genomic 3' untranslated sequence of neuroD was inserted into the vector backbone between into the Xho I and Not I sites.

To prepare an Eco RI-Xba I fragment containing neuroD promoter sequences joined to the β-galactosidase gene, a 1.4 kb Eco RI(vector-derived)-Asp718 fragment containing the 5' untranslated murine neuroD genomic sequence was ligated to a Hind III-Xba I fragment containing the cytoplasmic β-galactosidase gene such that the Asp 718 and Hind III sites were destroyed. The resulting approximately 4.4 kb Eco RI-Xba I fragment, containing the 5' neuroD genomic sequence (including the neuroD promoter) and the β-galactosidase gene in the same transcriptional orientation, was inserted into Eco RI-Xba I linearized pPNT to yield the plasmid pPNT/5'+β-gal. A neuroD fragment containing 3' untranslated DNA was obtained from a murine neuroD genomic clone that had been digested with Spe I and Not I(vector-derived) to yield an 8 kb fragment. To obtain a 5' Xho I site, the 8 kb fragment was inserted into Spe I-Not I linearized pBlueslcriptSK+(Stratagene), and the resulting plasmid digested with Xho I and Not I to obtain the 8 kb neuroD 3' genomic fragment. The Xho I-Not I fragment was inserted into Xho I-Not I linearized pPNT/5'+β-gal to yield the neuroD targeting vector. The final construct contained the 5' neuroD fragment, the β-galactosidase gene, and the 3' genomic neuroD fragment in the same orientation, and the hsv-tk and neomycin resistance genes in the opposite orientation.

The targeting construct was transfected by electroporation into mouse embryonic stem (ES) cells. A 129/Sv derived ES cell line, AK-7 described by Zhuang et at. (ibid.) was used for electroporation. These ES cells were routinely cultured on mitomycin C-treated (Sigma) SNL 76/7 cells (feeder cells) as described by McMahon and Bradley (Cell 62: 1073–1085, 1990; which is incorporated herein by reference in its entirety) in culture medium containing high glucose DMEM supplemented with 15% fetal bovine serum (Hyclone) and 0. 1 µM β-mercaptoethanol. To prepare the targeting construct for transfection, 25 µg of the targeting construct was linearized by digestion with Not I, phenol-chloroform extracted, and ethanol precipitated. The linearized vector was then electroporated into 1–2×10$^7$ AK-7 (ES) cells. The electroporated cells were seeded onto three 10-cm plates, with one plate receiving 50% of the electroporated cells and the remaining two plates each receiving 25% of the electroporated cells. After 24 hours, G418 was added to each of the plates to a final concentration of 150 µ/ml. After an additional 24 hours, gancyclovir was added to a final concentration of 0.2 µM to the 50% plate and one of the 25% plates. The third plate containing 25% of the electroporated cells was subjected to only G418 selection to assess the efficiency of gancyclovir selection. The culture medium for each plate was changed every day for the first few days, and then changed as needed after selection had occurred. After 10 days of selection, a portion of each colony was picked microscopically with a drawn micropipette, and was directly analyzed by PCR as described by Joyner et al. (*Nature* 338: 153–156, 1989; which is incorporated herein by reference in its entirety). Briefly, PCR amplification was performed as described (Kogan et at., *New England J. Med.* 317: 985–990, 1987; which is incorporated herein by reference in its entirety) using 40 cycles of 93° C. for 30 seconds, 57° C. for 30 seconds, and 65° C. for 3 minutes. To detect the wild-type allele, primers JL34 and JL36 (SEQ ID NOS:18 and 19, respectively) were used in the PCR reaction, to detect the mutant neuroD allele, primers JL34 and JL40 (SEQ ID NOS:18 and 20, respectively) were used in the PCR reaction. Positive colonies, identified by PCR, were subcloned into 4-well plates, expanded into 60 turn plates and frozen into 2–3 ampules.

Among the clones that were selected for both G418-resistance (positive selection for neo gene expression) and gancyclovir-resistance (negative selection for hsv-tk gene expression), 10% of the population contained correctly targeted integration of the vector into the murine neuroD locus (an overall 10% targeting frequency) The negative selection provided 4–3 fold enrichment for homologous recombination events.

To generate chimeric mice, each positive clone was thawed and passaged once on feeder cells. The transfected cells were trypsinized into single cells, and blastocysts obtained from C57BL/6J mice were injected with approximately 15 cells. The injected blastocysts were then implanted into pseudopregnant mice (C57BL/6J×CBA). Four male chimeras arose from the injected blastocysts (AK-71, AK-72, AK-74 and AK-75). The male chimeras AK-71 and AK-72 gave germ-line transmission at a high rate as determined by the frequency of agouti coat color transmission to their offspring (F1) in a cross with C57BL/6J female mice. Since 50% of the agouti coat color offspring (F1) should represent heterozygous mutants, their genotypes were determined by Southern blot analysis. Briefly, genomic DNA prepared from tail biopsies was digested with Eco RI and probed with the 1.4 kb 5' genomic sequence used to make the targeting construct. This probe detects a 4 kb Eco RI fragment from the wild-type allele and a 6.3 kb Eco RI fragment from the mutant allele. Therefore, a Southern analysis would show a single 4 kb band for a wild-type mouse, 4 kb and 6.3 kb fragments for a heterozygous mouse, and a single 6.3 kb band for a homozygous mutant mouse.

The resulting offspring (F1) heterozygous (±) mice, were mated with sibling heterozygous mice to give rise to the homozygous (−/−) mutant mice.

To study neuroD expression patterns in embryonic mice, chimeric mice or F1 heterozygous progeny from the chimera x C57B/6J mating were crossed with C57B/6J. Litters resulting from these crosses were harvested from pregnant females and stained for β-galactosidase activity. The embryos were dissected away from all the extra-embryonic tissue and the yolk sac was reserved for DNA analysis. The embryos were fixed for one hour in a Fix solution (0.1M phosphate buffer containing 0.2% glutaraldehyde, 2% formaldehyde, 5 mM EGTA )pH 7.3), 2 mM $MgCl_2$). The fixing solution was removed by three thirty-minute rinses with rinse solution (0.1M phosphate buffer (pH 7.3) containing 2 mM $MgCl_2$, 0.1% sodium deoxycholate, 0.2% NP-40). The fixed embryos were stained overnight in the dark in rinse solution containing 1 mg/ml X-gal, 5 mM sodium ferricyanide, 5 mM sodium ferrocyanide. After staining, the embryos were rinsed with PBS and stored in the Fix solution before preparation for examination. Examination of stained tissue from fetal and postnatal mice heterozygous for the mutation confirmed neuroD expression pattern in neuronal cells demonstrated by in situ hybridization (Example 4) and also demonstrated neuroD expression in the pancreas and gastrointestinal tract.

Blood glucose levels were detected using PRECISION QID blood glucose test strips and a PRECISION QID blood glucose sensor (Medisens Inc., Waltham, Mass.) according to the manufacturer's instruction. A tissue sample was taken for DNA analysis and the pups were fixed for further histological examination. Blood glucose levels in mice homozygous for the mutation (neuroD) had blood glucose levels between 2 and 3 times higher than the blood glucose level of wild-type mice. Heterozygous mutants exhibited similar blood glucose levels as wild-type mice. Mice that were homozygous for the mutation (lacking neuroD) had diabetes as demonstrated by high blood glucose levels and died by day four; some homozygous mice died at birth.

From the foregoing it will be appreciated that, although specific embodiments of the invention have been described herein for purposes of illustration, various modification may be made without deviating from the spirit and scope of the invention.

The embodiments of the invention in which an exclusive property or privilege is claimed are defined as follows:

1. An isolated nucleic acid molecule which hybridizes under stringent conditions with a nucleic acid molecule selected from among SEQ ID NO:1, SEQ ID NO:3, SEQ ID NO:8, SEQ ID NO:10, SEQ ID NO:12, SEQ ID NO:14, SEQ ID NO:16, and complements thereof.

2. A vector comprising in serial array a promoter, and the nucleic acid molecule of claim 1.

3. A cell in culture transformed by the nucleic acid molecule of claim 1.

4. A method for inducing differentiation of a non-neuronal cell in culture into a neuron, comprising introducing a nucleic acid molecule of claim 1 into the non-neuronal cell.

5. An isolated nucleic acid molecule, wherein the nucleic acid molecule encodes a polypeptide having an amino acid sequence selected from among the group consisting of SEQ ID NO:2, SEQ ID NO:4, SEQ ID NO:9, SEQ ID NO:11, SEQ ID NO:13, SEQ ID NO:15, and SEQ ID NO:17.

6. A vector comprising in serial array a promoter, and the nucleic acid molecule of claim 5.

7. A cell in culture transformed by the nucleic acid molecule of claim 5.

8. A method for inducing differentiation of a non-neuronal cell in culture into a neuronal cell in culture into a neuronal cell, comprising introducing the nucleic acid molecule of claim 5, into the non-neuronal cell.

* * * * *

UNITED STATES PATENT AND TRADEMARK OFFICE
CERTIFICATE OF CORRECTION

PATENT NO. : 5,695,995                      Page 1 of 5
DATED : December 9, 1997
INVENTOR(S) : H.M. Weintraub et al.

It is certified that error appears in the above-identified patent and that said Letters Patent is hereby corrected as shown below:

| COLUMN | LINE | |
|---|---|---|
| [56] Pg. 1, col. 1 | Refs. Cited (Other Pubs., Item 2) | "a basic" should read --a Basic-- |
| [56] Pg. 1, col. 1 | Refs. Cited (Other Pubs., Item 7) | *"embryos regulate the nuclear localization of XMyoD"* should not appear in character italics |
| 1 | 22 | "homodimeric" should read --heterodimeric-- |
| 2 | 18 | both occurrences of "amine" should read --amino-- |
| 2 | 20 | "amine" should read --amino-- |
| 2 | 23 | "amine" should read --amino-- |
| 2 | 26 | "amine" should read --amino-- |
| 2 | 29 | "amine" should read --amino-- |
| 2 | 34 | "amine" should read --amino-- |
| 2 | 38 | "amine" should read --amino-- |
| 2 | 40 | "amine" should read --amino-- |

UNITED STATES PATENT AND TRADEMARK OFFICE
CERTIFICATE OF CORRECTION

PATENT NO.   : 5,695,995
DATED        : December 9, 1997
INVENTOR(S)  : H.M. Weintraub et al.

It is certified that error appears in the above-identified patent and that said Letters Patent is hereby corrected as shown below:

| COLUMN | LINE | |
|---|---|---|
| 2 | 43 | "amine" should read --amino-- |
| 3 | 13 | "SEQ D" should read --SEQ ID-- |
| 5 | 21 | "ceding" should read --coding-- |
| 5 | 56 | between "precipitation" and "Wigler" insert --(-- |
| 5 | 59 | "electropotation" should read --electroporation-- |
| 5 | 63 | "vital" should read --viral-- |
| 7 | 4 | "an realizes" should read --art realizes-- |
| 7 | 20 | "4-6x" should read --4-6 X--, --0.1 X--, --2-6 X-- & --0.1 X--. |
| 7 | 22 | "0.1x" should read --4-6 X--, --0.1 X--, --2-6 X-- & --0.1 X--. |
| 7 | 26 | "2-6x" should read --4-6 X--, --0.1 X--, --2-6 X-- & --0.1 X--. |
| 7 | 28 | "0.1x" should read --4-6 X--, --0.1 X--, --2-6 X-- & --0.1 X--. |
| 7 | 37 | "theft" should read --their-- |
| 7 | 65 | "anti sense" should read --antisense-- |
| 8 | 61 | "et at." should read --et al.-- |
| 13 | 14 | "libray" should read --library-- |

UNITED STATES PATENT AND TRADEMARK OFFICE
CERTIFICATE OF CORRECTION

PATENT NO. : 5,695,995

DATED : December 9, 1997

INVENTOR(S) : H.M. Weintraub et al.

It is certified that error appears in the above-identified patent and that said Letters Patent is hereby corrected as shown below:

| COLUMN | LINE | |
|---|---|---|
| 13 | 35, | "Bgl H" to – Bgl II— |
| 13 | 47 | "Hind HI" should read --Hind III-- |
| 14 | 12 | "*strain L40*" should not appear in character italics |
| 14 | 41 | "pKS⁺m7a" should read --pKS⁺ m7a-- |
| 14 | 45 | "pKS m7a" should read --pKS⁺ m7a-- |
| 15 | 3 | "add" should read --acid-- |
| 15 | 10 | "HLH" should read --HLH,-- |
| 15 | 12 | "adds" should read --acids-- |
| 17 | 54 | "amine" should read --amino-- |
| 17 | 67 | "Development" should appear in character italics |
| 19 | 55 | "et at." should read --et al.-- |
| 19 | 58 | "et at." should read --et al.-- |
| 19 | 59 | "et at." should read --et al.-- |
| 20 | 4 | "et at." should read --et al.-- |
| 20 | 13 | "sting" should read --staining-- |

UNITED STATES PATENT AND TRADEMARK OFFICE
CERTIFICATE OF CORRECTION

PATENT NO. : 5,695,995
DATED : December 9, 1997
INVENTOR(S) : H.M. Weintraub et al.

It is certified that error appears in the above-indentified patent and that said Letters Patent is hereby corrected as shown below:

| COLUMN | LINE | |
|---|---|---|
| 22 | 1 | "*E coli*" should read --*E. coli*-- |
| 22 | 2 | insert a character space after "MgSO₄" |
| 22 | 50 | "1: 2301" should read --12301-- |
| 22 | 55 | "1.5" should read --1.6-- |
| 22 | 65 | "14B 1" should read --14B1-- |
| 23 | 22 | "14B 1" should read --14B1-- |
| 24 | 52 | "Alter" should read --After-- |
| 25 | 32 | "et at." should read --et al.-- |
| 25 | 65 | "et at." should read --et al.-- |
| 26 | 3 | "et at." should read --et al.-- |
| 26 | 7 | "hsv-tk," should read --hsv-tk;-- |
| 26 | 17 | "Asp718" should read --Asp 718-- |
| 26 | 31 | "pBlueslcriptSK" should read --pBlueskriptSK-- |
| 26 | 42 | "et at." should read --et al.-- |
| 27 | 4 | "et at." should read --et al.-- |

UNITED STATES PATENT AND TRADEMARK OFFICE
CERTIFICATE OF CORRECTION

PATENT NO. : 5,695,995
DATED : December 9, 1997
INVENTOR(S) : H.M. Weintraub et al.

It is certified that error appears in the above-identified patent and that said Letters Patent is hereby corrected as shown below:

| COLUMN | LINE | |
|---|---|---|
| 27 | 13 | "turn" should read --mm-- |
| 27 | 21 | "4-3" should read --4-8-- |
| 28 | 14 | ")pH" should read --(pH-- |
| 28 | 33 | "neuroD" should read --neuroD⁻-- |
| 58 (Claim 8, | 50 line 4) | delete "into a neuronal cell in culture" |
| 58 (Claim 8, | 52 line 4) | after "5" delete the "," |

Signed and Sealed this

Nineteenth Day of January, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 2089 base pairs
( B ) TYPE: nucleic acid
( C ) STRANDEDNESS: double
( D ) TOPOLOGY: linear ( i i ) MOLECULE TYPE: cDNA ( v i ) ORIGINAL SOURCE:
( A ) ORGANISM: Mus musculus ( i x ) FEATURE:
( A ) NAME/KEY: CDS
( B ) LOCATION: 229..1302

( x i ) SEQUENCE DESCRIPTION: SEQ ID NO:1:

```
ACTACGCAGC ACCGAGGTAC AGACACGCCA GCATGAAGCA CTGCGTTTAA CTTTTCCTGG        60

AGGCATCCAT TTTGCAGTGG ACTCCTGTGT ATTTCTATTT GTGTGCATTT CTGTAGGATT       120

AGGGAGAGGG AGCTGAAGGC TTATCCAGCT TTTAAATATA GCGGGTGGAT TTCCCCCCCT       180

TTCTTCTTCT GCTTGCCTCT CTCCCTGTTC AATACAGGAA GTGGAAAC ATG ACC AAA        237
                                                    Met Thr Lys
                                                      1
```

| TCA | TAC | AGC | GAG | AGC | GGG | CTG | ATG | GGC | GAG | CCT | CAG | CCC | CAA | GGT | CCC | 285 |
|-----|-----|-----|-----|-----|-----|-----|-----|-----|-----|-----|-----|-----|-----|-----|-----|-----|
| Ser | Tyr | Ser | Glu | Ser | Gly | Leu | Met | Gly | Glu | Pro | Gln | Pro | Gln | Gly | Pro | |
|     | 5   |     |     |     |     | 10  |     |     |     |     | 15  |     |     |     |     | |

| CCA | AGC | TGG | ACA | GAT | GAG | TGT | CTC | AGT | TCT | CAG | GAC | GAG | GAA | CAC | GAG | 333 |
|-----|-----|-----|-----|-----|-----|-----|-----|-----|-----|-----|-----|-----|-----|-----|-----|-----|
| Pro | Ser | Trp | Thr | Asp | Glu | Cys | Leu | Ser | Ser | Gln | Asp | Glu | Glu | His | Glu | |
| 20  |     |     |     |     | 25  |     |     |     |     | 30  |     |     |     |     | 35  | |

| GCA | GAC | AAG | AAA | GAG | GAC | GAG | CTT | GAA | GCC | ATG | AAT | GCA | GAG | GAG | GAC | 381 |
|-----|-----|-----|-----|-----|-----|-----|-----|-----|-----|-----|-----|-----|-----|-----|-----|-----|
| Ala | Asp | Lys | Lys | Glu | Asp | Glu | Leu | Glu | Ala | Met | Asn | Ala | Glu | Glu | Asp | |
|     |     | 40  |     |     |     |     | 45  |     |     |     |     | 50  |     |     |     | |

| TCT | CTG | AGA | AAC | GGG | GGA | GAG | GAG | GAG | GAA | GAT | GAG | GAT | CTA | GAG |     | 429 |
|-----|-----|-----|-----|-----|-----|-----|-----|-----|-----|-----|-----|-----|-----|-----|-----|-----|
| Ser | Leu | Arg | Asn | Gly | Gly | Glu | Glu | Glu | Glu | Asp | Glu | Asp | Leu | Glu | | |
|     |     | 55  |     |     |     |     | 60  |     |     |     |     | 65  |     |     | | |

| GAA | GAG | GAG | GAA | GAA | GAA | GAG | GAG | GAG | GAG | GAT | CAA | AAG | CCC | AAG | AGA | 477 |
|-----|-----|-----|-----|-----|-----|-----|-----|-----|-----|-----|-----|-----|-----|-----|-----|-----|
| Glu | Glu | Glu | Glu | Glu | Glu | Glu | Glu | Glu | Glu | Asp | Gln | Lys | Pro | Lys | Arg | |
|     | 70  |     |     |     |     | 75  |     |     |     |     | 80  |     |     |     |     | |

| CGG | GGT | CCC | AAA | AAG | AAA | AAG | ATG | ACC | AAG | GCG | CGC | CTA | GAA | CGT | TTT | 525 |
|-----|-----|-----|-----|-----|-----|-----|-----|-----|-----|-----|-----|-----|-----|-----|-----|-----|
| Arg | Gly | Pro | Lys | Lys | Lys | Lys | Met | Thr | Lys | Ala | Arg | Leu | Glu | Arg | Phe | |
|     | 85  |     |     |     |     | 90  |     |     |     |     | 95  |     |     |     |     | |

| AAA | TTA | AGG | CGC | ATG | AAG | GCC | AAC | GCC | CGC | GAG | CGG | AAC | CGC | ATG | CAC | 573 |
|-----|-----|-----|-----|-----|-----|-----|-----|-----|-----|-----|-----|-----|-----|-----|-----|-----|
| Lys | Leu | Arg | Arg | Met | Lys | Ala | Asn | Ala | Arg | Glu | Arg | Asn | Arg | Met | His | |
| 100 |     |     |     |     | 105 |     |     |     |     | 110 |     |     |     |     | 115 | |

| GGG | CTG | AAC | GCG | GCG | CTG | GAC | AAC | CTG | CGC | AAG | GTG | GTA | CCT | TGC | TAC | 621 |
|-----|-----|-----|-----|-----|-----|-----|-----|-----|-----|-----|-----|-----|-----|-----|-----|-----|
| Gly | Leu | Asn | Ala | Ala | Leu | Asp | Asn | Leu | Arg | Lys | Val | Val | Pro | Cys | Tyr | |
|     |     |     | 120 |     |     |     |     | 125 |     |     |     |     | 130 |     |     | |

| TCC | AAG | ACC | CAG | AAA | CTG | TCT | AAA | ATA | GAG | ACA | CTG | CGC | TTG | GCC | AAG | 669 |
|-----|-----|-----|-----|-----|-----|-----|-----|-----|-----|-----|-----|-----|-----|-----|-----|-----|
| Ser | Lys | Thr | Gln | Lys | Leu | Ser | Lys | Ile | Glu | Thr | Leu | Arg | Leu | Ala | Lys | |
|     |     |     | 135 |     |     |     |     | 140 |     |     |     |     | 145 |     |     | |

| AAC | TAC | ATC | TGG | GCT | CTG | TCA | GAG | ATC | CTG | CGC | TCA | GGC | AAA | AGC | CCT | 717 |
|-----|-----|-----|-----|-----|-----|-----|-----|-----|-----|-----|-----|-----|-----|-----|-----|-----|
| Asn | Tyr | Ile | Trp | Ala | Leu | Ser | Glu | Ile | Leu | Arg | Ser | Gly | Lys | Ser | Pro | |
|     |     | 150 |     |     |     |     | 155 |     |     |     |     | 160 |     |     |     | |

| GAT | CTG | GTC | TCC | TTC | GTA | CAG | ACG | CTC | TGC | AAA | GGT | TTG | TCC | CAG | CCC | 765 |
|-----|-----|-----|-----|-----|-----|-----|-----|-----|-----|-----|-----|-----|-----|-----|-----|-----|
| Asp | Leu | Val | Ser | Phe | Val | Gln | Thr | Leu | Cys | Lys | Gly | Leu | Ser | Gln | Pro | |
|     | 165 |     |     |     |     | 170 |     |     |     |     | 175 |     |     |     |     | |

| ACT | ACC | AAT | TTG | GTC | GCC | GGC | TGC | CTG | CAG | CTC | AAC | CCT | CGG | ACT | TTC | 813 |
|-----|-----|-----|-----|-----|-----|-----|-----|-----|-----|-----|-----|-----|-----|-----|-----|-----|
| Thr | Thr | Asn | Leu | Val | Ala | Gly | Cys | Leu | Gln | Leu | Asn | Pro | Arg | Thr | Phe | |
| 180 |     |     |     |     | 185 |     |     |     |     | 190 |     |     |     |     | 195 | |

| TTG | CCT | GAG | CAG | AAC | CCG | GAC | ATG | CCC | CCG | CAT | CTG | CCA | ACC | GCC | AGC | 861 |
|-----|-----|-----|-----|-----|-----|-----|-----|-----|-----|-----|-----|-----|-----|-----|-----|-----|
| Leu | Pro | Glu | Gln | Asn | Pro | Asp | Met | Pro | Pro | His | Leu | Pro | Thr | Ala | Ser | |
|     |     |     |     | 200 |     |     |     |     | 205 |     |     |     |     | 210 |     | |

| GCT | TCC | TTC | CCG | GTG | CAT | CCC | TAC | TCC | TAC | CAG | TCC | CCT | GGA | CTG | CCC | 909 |
|-----|-----|-----|-----|-----|-----|-----|-----|-----|-----|-----|-----|-----|-----|-----|-----|-----|
| Ala | Ser | Phe | Pro | Val | His | Pro | Tyr | Ser | Tyr | Gln | Ser | Pro | Gly | Leu | Pro | |
|     |     |     | 215 |     |     |     |     | 220 |     |     |     |     | 225 |     |     | |

| AGC | CCG | CCC | TAC | GGC | ACC | ATG | GAC | AGC | TCC | CAC | GTC | TTC | CAC | GTC | AAG | 957 |
|-----|-----|-----|-----|-----|-----|-----|-----|-----|-----|-----|-----|-----|-----|-----|-----|-----|
| Ser | Pro | Pro | Tyr | Gly | Thr | Met | Asp | Ser | Ser | His | Val | Phe | His | Val | Lys | |
|     |     | 230 |     |     |     |     | 235 |     |     |     |     | 240 |     |     |     | |

| CCG | CCG | CCA | CAC | GCC | TAC | AGC | GCA | GCT | CTG | GAG | CCC | TTC | TTT | GAA | AGC | 1005 |
|-----|-----|-----|-----|-----|-----|-----|-----|-----|-----|-----|-----|-----|-----|-----|-----|------|
| Pro | Pro | Pro | His | Ala | Tyr | Ser | Ala | Ala | Leu | Glu | Pro | Phe | Phe | Glu | Ser | |
|     | 245 |     |     |     |     | 250 |     |     |     |     | 255 |     |     |     |     | |

| CCC | CTA | ACT | GAC | TGC | ACC | AGC | CCT | TCC | TTT | GAC | GGA | CCC | CTC | AGC | CCG | 1053 |
|-----|-----|-----|-----|-----|-----|-----|-----|-----|-----|-----|-----|-----|-----|-----|-----|------|
| Pro | Leu | Thr | Asp | Cys | Thr | Ser | Pro | Ser | Phe | Asp | Gly | Pro | Leu | Ser | Pro | |
| 260 |     |     |     |     | 265 |     |     |     |     | 270 |     |     |     |     | 275 | |

-continued

| | | | | | | | | | | | | | | | | |
|---|---|---|---|---|---|---|---|---|---|---|---|---|---|---|---|---|
| CCG | CTC | AGC | ATC | AAT | GGC | AAC | TTC | TCT | TTC | AAA | CAC | GAA | CCA | TCC | GCC | 1101 |
| Pro | Leu | Ser | Ile | Asn<br>280 | Gly | Asn | Phe | Ser | Phe<br>285 | Lys | His | Glu | Pro | Ser<br>290 | Ala | |
| GAG | TTT | GAA | AAA | AAT | TAT | GCC | TTT | ACC | ATG | CAC | TAC | CCT | GCA | GCG | ACG | 1149 |
| Glu | Phe | Glu | Lys<br>295 | Asn | Tyr | Ala | Phe | Thr<br>300 | Met | His | Tyr | Pro | Ala<br>305 | Ala | Thr | |
| CTG | GCA | GGG | CCC | CAA | AGC | CAC | GGA | TCA | ATC | TTC | TCT | TCC | GGT | GCC | GCT | 1197 |
| Leu | Ala | Gly<br>310 | Pro | Gln | Ser | His | Gly<br>315 | Ser | Ile | Phe | Ser | Ser<br>320 | Gly | Ala | Ala | |
| GCC | CCT | CGC | TGC | GAG | ATC | CCC | ATA | GAC | AAC | ATT | ATG | TCT | TTC | GAT | AGC | 1245 |
| Ala | Pro | Arg<br>325 | Cys | Glu | Ile | Pro<br>330 | Ile | Asp | Asn | Ile | Met<br>335 | Ser | Phe | Asp | Ser | |
| CAT | TCG | CAT | CAT | GAG | CGA | GTC | ATG | AGT | GCC | CAG | CTT | AAT | GCC | ATC | TTT | 1293 |
| His<br>340 | Ser | His | His | Glu | Arg<br>345 | Val | Met | Ser | Ala | Gln<br>350 | Leu | Asn | Ala | Ile | Phe<br>355 | |
| CAC | GAT | TAGAGGGCAC | GTCAGTTTCA | CTATTCCCGG | GAAACGAATC | CACTGTGCGT | | | | | | | | | | 1349 |
| His | Asp | | | | | | | | | | | | | | | |

| | | | | | |
|---|---|---|---|---|---|
| ACAGTGACTG | TCCTGTTTAC | AGAAGGCAGC | CCTTTTGCTA | AGATTGCTGC | AAAGTGCAAA | 1409 |
| TACTCAAAGC | TTCAAGTGAT | ATATGTATTT | ATTGTCGTTA | CTGCCTTTGG | AAGAAACAGG | 1469 |
| GGATCAAAGT | TCCTGTTCAC | CTTATGTATT | GTTTCTATA | GCTCTTCTAT | TTTAAAAATA | 1529 |
| ATAATACAGT | AAAGTAAAAA | AGAAAATGTG | TACCACGAAT | TCGTGTAGC | TGTATTCAGA | 1589 |
| TCGTATTAAT | TATCTGATCG | GGATAAAAAA | AATCACAAGC | AATAATTAGG | ATCTATGCAA | 1649 |
| TTTTTAAACT | AGTAATGGGC | CAATTAAAAT | ATATATAAAT | ATATATTTT | CAACCAGCAT | 1709 |
| TTTACTACCT | GTGACCTTTC | CCATGCTGAA | TTATTTGTT | GTGATTTGT | ACAGAATTTT | 1769 |
| TAATGACTTT | TTATAACGTG | GATTCCTAT | TTAAAACCA | TGCAGCTTCA | TCAATTTTA | 1829 |
| TACATATCAG | AAAAGTAGAA | TTATATCTAA | TTTATACAAA | ATAATTTAAC | TAATTTAAAC | 1889 |
| CAGCAGAAAA | GTGCTTAGAA | AGTTATTGCG | TTGCCTTAGC | ACTTCTTTCT | TCTCTAATTG | 1949 |
| TAAAAAGAA | AAAAAAAAA | AAAAACTCG | AGGGGGGGCC | CGGTACCCAG | CTTTTGTTCC | 2009 |
| CTTAGTGAG | GGTTAATTGC | GCGCTTGGCG | TAATCATGGT | CATAGCTGTT | TCCTGTGTGA | 2069 |
| ATTGTTATCC | GCTCACAATT | | | | | 2089 |

(2) INFORMATION FOR SEQ ID NO:2:

(i) SEQUENCE CHARACTERISTICS:
(A) LENGTH: 357 amino acids
(B) TYPE: amino acid
(D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met<br>1 | Thr | Lys | Ser | Tyr<br>5 | Ser | Glu | Ser | Gly | Leu<br>10 | Met | Gly | Glu | Pro<br>15 | Gln | Pro |
| Gln | Gly | Pro | Pro<br>20 | Ser | Trp | Thr | Asp | Glu<br>25 | Cys | Leu | Ser | Ser | Gln<br>30 | Asp | Glu |
| Glu | His | Glu<br>35 | Ala | Asp | Lys | Lys | Glu<br>40 | Asp | Glu | Leu | Glu | Ala<br>45 | Met | Asn | Ala |
| Glu | Glu<br>50 | Asp | Ser | Leu | Arg | Asn<br>55 | Gly | Gly | Glu | Glu | Glu<br>60 | Glu | Glu | Asp | Glu |
| Asp<br>65 | Leu | Glu | Glu | Glu | Glu<br>70 | Glu | Glu | Glu | Glu | Glu<br>75 | Glu | Glu | Asp | Gln | Lys<br>80 |
| Pro | Lys | Arg | Arg | Gly<br>85 | Pro | Lys | Lys | Lys | Met<br>90 | Thr | Lys | Ala | Arg | Leu<br>95 | |

```
Glu  Arg  Phe  Lys  Leu  Arg  Arg  Met  Lys  Ala  Asn  Ala  Arg  Glu  Arg  Asn
               100                 105                      110

Arg  Met  His  Gly  Leu  Asn  Ala  Ala  Leu  Asp  Asn  Leu  Arg  Lys  Val  Val
               115                 120                      125

Pro  Cys  Tyr  Ser  Lys  Thr  Gln  Lys  Leu  Ser  Lys  Ile  Glu  Thr  Leu  Arg
               130                 135                      140

Leu  Ala  Lys  Asn  Tyr  Ile  Trp  Ala  Leu  Ser  Glu  Ile  Leu  Arg  Ser  Gly
145                      150                      155                      160

Lys  Ser  Pro  Asp  Leu  Val  Ser  Phe  Val  Gln  Thr  Leu  Cys  Lys  Gly  Leu
               165                      170                      175

Ser  Gln  Pro  Thr  Thr  Asn  Leu  Val  Ala  Gly  Cys  Leu  Gln  Leu  Asn  Pro
               180                      185                      190

Arg  Thr  Phe  Leu  Pro  Glu  Gln  Asn  Pro  Asp  Met  Pro  Pro  His  Leu  Pro
               195                      200                      205

Thr  Ala  Ser  Ala  Ser  Phe  Pro  Val  His  Pro  Tyr  Ser  Tyr  Gln  Ser  Pro
          210                      215                      220

Gly  Leu  Pro  Ser  Pro  Pro  Tyr  Gly  Thr  Met  Asp  Ser  Ser  His  Val  Phe
225                      230                      235                      240

His  Val  Lys  Pro  Pro  Pro  His  Ala  Tyr  Ser  Ala  Ala  Leu  Glu  Pro  Phe
               245                      250                      255

Phe  Glu  Ser  Pro  Leu  Thr  Asp  Cys  Thr  Ser  Pro  Ser  Phe  Asp  Gly  Pro
               260                      265                      270

Leu  Ser  Pro  Pro  Leu  Ser  Ile  Asn  Gly  Asn  Phe  Ser  Phe  Lys  His  Glu
               275                      280                      285

Pro  Ser  Ala  Glu  Phe  Glu  Lys  Asn  Tyr  Ala  Phe  Thr  Met  His  Tyr  Pro
     290                      295                      300

Ala  Ala  Thr  Leu  Ala  Gly  Pro  Gln  Ser  His  Gly  Ser  Ile  Phe  Ser  Ser
305                      310                      315                      320

Gly  Ala  Ala  Ala  Pro  Arg  Cys  Glu  Ile  Pro  Ile  Asp  Asn  Ile  Met  Ser
               325                      330                      335

Phe  Asp  Ser  His  Ser  His  His  Glu  Arg  Val  Met  Ser  Ala  Gln  Leu  Asn
               340                      345                      350

Ala  Ile  Phe  His  Asp
               355
```

(2) INFORMATION FOR SEQ ID NO:3:

(i) SEQUENCE CHARACTERISTICS:
        (A) LENGTH: 1275 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Xenopus laevis (ix) FEATURE:
        (A) NAME/KEY: CDS
        (B) LOCATION: 25..1083

(xi) SEQUENCE DESCRIPTION: SEQ ID NO:3:

```
ATTTCCTTTC TCCAGATCTA AAAA ATG ACC AAA TCG TAT GGA GAG AAT GGG          51
                          Met Thr Lys Ser Tyr Gly Glu Asn Gly
                           1               5

CTG ATC CTG GCC GAG ACT CCG GGC TGC AGA GGA TGG GTG GAC GAA TGC         99
Leu Ile Leu Ala Glu Thr Pro Gly Cys Arg Gly Trp Val Asp Glu Cys
 10              15                  20                      25

CTG AGT TCT CAG GAT GAA AAC GAT CTG GAG AAA AAG GAG GGA GAG TTG        147
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Leu | Ser | Ser | Gln | Asp<br>30 | Glu | Asn | Asp | Leu | Glu<br>35 | Lys | Lys | Glu | Gly | Glu<br>40 | Leu | |

| ATG | AAA | GAA | GAC | GAT | GAA | GAC | TCA | CTG | AAT | CAT | CAC | AAT | GGA | GAG | GAG | 195 |
|-----|-----|-----|-----|-----|-----|-----|-----|-----|-----|-----|-----|-----|-----|-----|-----|-----|
| Met | Lys | Glu | Asp | Asp<br>45 | Glu | Asp | Ser | Leu | Asn<br>50 | His | His | Asn | Gly | Glu<br>55 | Glu | |

| AAC | GAG | GAA | GAG | GAT | GAA | GGG | GAT | GAG | GAG | GAG | GAG | GAC | GAT | GAA | GAT | 243 |
|-----|-----|-----|-----|-----|-----|-----|-----|-----|-----|-----|-----|-----|-----|-----|-----|-----|
| Asn | Glu | Glu | Glu<br>60 | Asp | Glu | Gly | Asp | Glu<br>65 | Glu | Glu | Glu | Asp | Asp<br>70 | Glu | Asp | |

| GAT | GAT | GAG | GAT | GAC | GAC | CAG | AAA | CCC | AAA | AGG | CGA | GGA | CCG | AAA | AAG | 291 |
|-----|-----|-----|-----|-----|-----|-----|-----|-----|-----|-----|-----|-----|-----|-----|-----|-----|
| Asp | Asp<br>75 | Glu | Asp | Asp | Asp | Gln<br>80 | Lys | Pro | Lys | Arg | Arg<br>85 | Gly | Pro | Lys | Lys | |

| AAA | AAA | ATG | ACG | AAA | GCC | CGG | GTG | GAG | CGA | TTT | AAA | GTG | AGA | CGC | ATG | 339 |
|-----|-----|-----|-----|-----|-----|-----|-----|-----|-----|-----|-----|-----|-----|-----|-----|-----|
| Lys | Lys<br>90 | Met | Thr | Lys | Ala<br>95 | Arg | Val | Glu | Arg | Phe<br>100 | Lys | Val | Arg | Arg | Met<br>105 | |

| AAG | GCA | AAC | GCC | AGG | GAG | AGG | AAT | CGC | ATG | CAC | GGA | CTC | AAC | GAT | GCC | 387 |
|-----|-----|-----|-----|-----|-----|-----|-----|-----|-----|-----|-----|-----|-----|-----|-----|-----|
| Lys | Ala | Asn | Ala | Arg<br>110 | Glu | Arg | Asn | Arg | Met<br>115 | His | Gly | Leu | Asn | Asp<br>120 | Ala | |

| CTG | GAC | AGT | CTG | CGC | AAA | GTT | GTG | CCC | TGC | TAC | TCC | AAA | ACA | CAA | AAG | 435 |
|-----|-----|-----|-----|-----|-----|-----|-----|-----|-----|-----|-----|-----|-----|-----|-----|-----|
| Leu | Asp | Ser | Leu<br>125 | Arg | Lys | Val | Val | Pro<br>130 | Cys | Tyr | Ser | Lys | Thr<br>135 | Gln | Lys | |

| TTG | TCT | AAG | ATT | GAA | ACT | CTG | CGC | CTG | GCT | AAG | AAC | TAC | ATC | TGG | GCT | 483 |
|-----|-----|-----|-----|-----|-----|-----|-----|-----|-----|-----|-----|-----|-----|-----|-----|-----|
| Leu | Ser | Lys | Ile | Glu<br>140 | Thr | Leu | Arg | Leu | Ala<br>145 | Lys | Asn | Tyr | Ile | Trp<br>150 | Ala | |

| CTT | TCT | GAG | ATT | TTA | AGG | TCC | GGC | AAA | AGC | CCA | GAC | CTG | GTG | TCC | TTT | 531 |
|-----|-----|-----|-----|-----|-----|-----|-----|-----|-----|-----|-----|-----|-----|-----|-----|-----|
| Leu | Ser | Glu | Ile | Leu<br>155 | Arg | Ser | Gly | Lys | Ser<br>160 | Pro | Asp | Leu | Val | Ser<br>165 | Phe | |

| GTA | CAA | ACT | CTC | TGC | AAA | GGT | TTG | TCG | CAG | CCC | ACC | ACC | AAT | CTA | GTA | 579 |
|-----|-----|-----|-----|-----|-----|-----|-----|-----|-----|-----|-----|-----|-----|-----|-----|-----|
| Val | Gln | Thr | Leu | Cys<br>170 | Lys | Gly | Leu | Ser<br>175 | Gln | Pro | Thr | Thr | Asn<br>180 | Leu | Val<br>185 | |

| GCG | GGG | TGT | CTG | CAG | CTG | AAC | CCC | AGA | ACT | TTC | CTT | CCT | GAG | CAG | AGT | 627 |
|-----|-----|-----|-----|-----|-----|-----|-----|-----|-----|-----|-----|-----|-----|-----|-----|-----|
| Ala | Gly | Cys | Leu | Gln | Leu<br>190 | Asn | Pro | Arg | Thr | Phe<br>195 | Leu | Pro | Glu | Gln | Ser<br>200 | |

| CAG | GAC | ATC | CAG | TCG | CAC | ATG | CAA | ACA | GCG | AGC | TCT | TCC | TTC | CCT | CTG | 675 |
|-----|-----|-----|-----|-----|-----|-----|-----|-----|-----|-----|-----|-----|-----|-----|-----|-----|
| Gln | Asp | Ile | Gln | Ser<br>205 | His | Met | Gln | Thr | Ala<br>210 | Ser | Ser | Ser | Phe | Pro<br>215 | Leu | |

| CAG | GGC | TAT | CCC | TAT | CAG | TCC | CCT | GGT | CTT | CCC | AGT | CCC | CCC | TAT | GGT | 723 |
|-----|-----|-----|-----|-----|-----|-----|-----|-----|-----|-----|-----|-----|-----|-----|-----|-----|
| Gln | Gly | Tyr | Pro | Tyr<br>220 | Gln | Ser | Pro | Gly | Leu<br>225 | Pro | Ser | Pro | Pro | Tyr<br>230 | Gly | |

| ACC | ATG | GAC | AGC | TCC | CAT | GTA | TTC | CAC | GTC | AAG | CCT | CAC | TCC | TAT | GGG | 771 |
|-----|-----|-----|-----|-----|-----|-----|-----|-----|-----|-----|-----|-----|-----|-----|-----|-----|
| Thr | Met | Asp | Ser<br>235 | Ser | His | Val | Phe | His<br>240 | Val | Lys | Pro | His | Ser<br>245 | Tyr | Gly | |

| GCG | GCC | CTG | GAG | CCT | TTC | TTT | GAC | AGC | AGC | ACC | GTC | ACT | GAG | TGT | ACC | 819 |
|-----|-----|-----|-----|-----|-----|-----|-----|-----|-----|-----|-----|-----|-----|-----|-----|-----|
| Ala | Ala | Leu | Glu<br>250 | Pro | Phe | Phe | Asp | Ser<br>255 | Ser | Thr | Val | Thr | Glu<br>260 | Cys | Thr<br>265 | |

| AGC | CCG | TCA | TTC | GAT | GGT | CCC | CTG | AGC | CCA | CCC | CTT | AGT | GTT | AAT | GGG | 867 |
|-----|-----|-----|-----|-----|-----|-----|-----|-----|-----|-----|-----|-----|-----|-----|-----|-----|
| Ser | Pro | Ser | Phe | Asp<br>270 | Gly | Pro | Leu | Ser | Pro<br>275 | Pro | Leu | Ser | Val | Asn<br>280 | Gly | |

| AAC | TTT | ACT | TTT | AAA | CAC | GAG | CAT | TCG | GAG | TAT | GAT | AAA | AAT | TAC | ACG | 915 |
|-----|-----|-----|-----|-----|-----|-----|-----|-----|-----|-----|-----|-----|-----|-----|-----|-----|
| Asn | Phe | Thr | Phe<br>285 | Lys | His | Glu | His | Ser<br>290 | Glu | Tyr | Asp | Lys | Asn<br>295 | Tyr | Thr | |

| TTC | ACT | ATG | CAC | TAT | CCT | GCA | GCC | ACT | ATA | TCC | CAG | GGC | CAC | GGA | CCA | 963 |
|-----|-----|-----|-----|-----|-----|-----|-----|-----|-----|-----|-----|-----|-----|-----|-----|-----|
| Phe | Thr | Met | His<br>300 | Tyr | Pro | Ala | Ala | Thr<br>305 | Ile | Ser | Gln | Gly | His<br>310 | Gly | Pro | |

| TTG | TTC | TCC | ACG | GGG | GGA | CCA | CGC | TGT | GAA | ATC | CCA | ATA | GAC | ACC | ATC | 1011 |
|-----|-----|-----|-----|-----|-----|-----|-----|-----|-----|-----|-----|-----|-----|-----|-----|------|
| Leu | Phe | Ser | Thr<br>315 | Gly | Gly | Pro | Arg | Cys<br>320 | Glu | Ile | Pro | Ile | Asp<br>325 | Thr | Ile | |

| ATG | TCC | TAT | GAC | GGT | CAC | TCC | CAC | CAT | GAA | AGA | GTC | ATG | AGT | GCC | CAG | 1059 |
|-----|-----|-----|-----|-----|-----|-----|-----|-----|-----|-----|-----|-----|-----|-----|-----|------|
| Met | Ser | Tyr | Asp<br>330 | Gly | His | Ser<br>335 | His | His | Glu | Arg | Val<br>340 | Met | Ser | Ala | Gln<br>345 | |

| CTA | AAT | GCC | ATC | TTT | CAT | GAT | TAACCCTTGG | AAGATCAAAA | CAACTGACTG | 1110 |
|-----|-----|-----|-----|-----|-----|-----|------------|------------|------------|------|

```
Leu Asn Ala Ile Phe His Asp
                350

TGCATTGCCA GGACTGTCTT GTTTACCAAG GGCAGACACG TGGGTAGTAA AAGTGCAAAT       1170

GCCCCACTCT GGGGCTGTAA CAAACTTGAT CTTGTCCTGC CTTTAGATAT GGGGAAACCT       1230

AATGTATTAA TTCCCACCTC CTTCCAATCG ACACTCCTTT AAATT                      1275
```

( 2 ) INFORMATION FOR SEQ ID NO:4:

( i ) SEQUENCE CHARACTERISTICS:
        ( A ) LENGTH: 352 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Lys Ser Tyr Gly Glu Asn Gly Leu Ile Leu Ala Glu Thr Pro
 1               5                  10                  15

Gly Cys Arg Gly Trp Val Asp Glu Cys Leu Ser Ser Gln Asp Glu Asn
            20                  25                  30

Asp Leu Glu Lys Lys Glu Gly Glu Leu Met Lys Glu Asp Asp Glu Asp
        35                  40                  45

Ser Leu Asn His His Asn Gly Glu Glu Asn Glu Glu Asp Glu Gly
    50                  55                  60

Asp Glu Glu Glu Glu Asp Asp Glu Asp Asp Asp Glu Asp Asp Asp Gln
65                  70                  75                  80

Lys Pro Lys Arg Arg Gly Pro Lys Lys Lys Lys Met Thr Lys Ala Arg
                85                  90                  95

Val Glu Arg Phe Lys Val Arg Arg Met Lys Ala Asn Ala Arg Glu Arg
            100                 105                 110

Asn Arg Met His Gly Leu Asn Asp Ala Leu Asp Ser Leu Arg Lys Val
            115                 120                 125

Val Pro Cys Tyr Ser Lys Thr Gln Lys Leu Ser Lys Ile Glu Thr Leu
        130                 135                 140

Arg Leu Ala Lys Asn Tyr Ile Trp Ala Leu Ser Glu Ile Leu Arg Ser
145                 150                 155                 160

Gly Lys Ser Pro Asp Leu Val Ser Phe Val Gln Thr Leu Cys Lys Gly
                165                 170                 175

Leu Ser Gln Pro Thr Thr Asn Leu Val Ala Gly Cys Leu Gln Leu Asn
            180                 185                 190

Pro Arg Thr Phe Leu Pro Glu Gln Ser Gln Asp Ile Gln Ser His Met
            195                 200                 205

Gln Thr Ala Ser Ser Ser Phe Pro Leu Gln Gly Tyr Pro Tyr Gln Ser
        210                 215                 220

Pro Gly Leu Pro Ser Pro Pro Tyr Gly Thr Met Asp Ser Ser His Val
225                 230                 235                 240

Phe His Val Lys Pro His Ser Tyr Gly Ala Ala Leu Glu Pro Phe Phe
                245                 250                 255

Asp Ser Ser Thr Val Thr Glu Cys Thr Ser Pro Ser Phe Asp Gly Pro
            260                 265                 270

Leu Ser Pro Pro Leu Ser Val Asn Gly Asn Phe Thr Phe Lys His Glu
        275                 280                 285

His Ser Glu Tyr Asp Lys Asn Tyr Thr Phe Thr Met His Tyr Pro Ala
    290                 295                 300

Ala Thr Ile Ser Gln Gly His Gly Pro Leu Phe Ser Thr Gly Gly Pro
305                 310                 315                 320
```

Arg Cys Glu Ile Pro Ile Asp Thr Ile Met Ser Tyr Asp Gly His Ser
              325                 330                 335

His His Glu Arg Val Met Ser Ala Gln Leu Asn Ala Ile Phe His Asp
            340                 345                 350

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

Asn Ala Arg Glu Arg Arg Arg
1               5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:6:

Asn Glu Arg Glu Arg Asn Arg
1               5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:7:

Asn Ala Arg Glu Arg
1               5

( 2 ) INFORMATION FOR SEQ ID NO:8:

( i ) SEQUENCE CHARACTERISTICS:
        ( A ) LENGTH: 524 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: 9F1

( i x ) FEATURE:
        ( A ) NAME/KEY: CDS
        ( B ) LOCATION: 57..524

( x i ) SEQUENCE DESCRIPTION: SEQ ID NO:8:

```
TTTTTCTGCT TTTCTTTCTG TTTGCCTCTC CCTTGTTGAA TGTAGGAAAT CGAAAC                    56

ATG ACC AAA TCG TAC AGC GAG AGT GGG CTG ATG GGC GAG CCT CAG CCC                 104
Met Thr Lys Ser Tyr Ser Glu Ser Gly Leu Met Gly Glu Pro Gln Pro
 1           5                   10                  15

CAA GGT CCT CCA AGC TGG ACA GAC GAG TGT CTC AGT TCT CAG GAC GAG                 152
Gln Gly Pro Pro Ser Trp Thr Asp Glu Cys Leu Ser Ser Gln Asp Glu
            20                  25                  30

GAG CAC GAG GCA GAC AAG AAG GAG GAC GAC CTC GAA GCC ATG AAC GCA                 200
Glu His Glu Ala Asp Lys Lys Glu Asp Asp Leu Glu Ala Met Asn Ala
        35                  40                  45

GAG GAG GAC TCA CTG AGG AAC GGG GGA GAG GAG GAG GAC GAA GAT GAG                 248
Glu Glu Asp Ser Leu Arg Asn Gly Gly Glu Glu Glu Asp Glu Asp Glu
    50                  55                  60

GAC CTG GAA GAG GAG GAA GAA GAG GAA GAG GAG GAT GAC GAT CAA AAG                 296
Asp Leu Glu Glu Glu Glu Glu Glu Glu Glu Glu Asp Asp Asp Gln Lys
65                  70                  75                  80

CCC AAG AGA CGC GGC CCC AAA AAG AAG AAG ATG ACT AAG GCT CGC CTG                 344
Pro Lys Arg Arg Gly Pro Lys Lys Lys Lys Met Thr Lys Ala Arg Leu
                85                  90                  95

GAG CGT TTT AAA TTG AGA CGC ATG AAG GCT AAC GCC CGG GAG CGG AAC                 392
Glu Arg Phe Lys Leu Arg Arg Met Lys Ala Asn Ala Arg Glu Arg Asn
            100                 105                 110

CGC ATG CAC GGA CTG AAC GCG GCG CTA GAC AAC CTG CGC AAG GTG GTG                 440
Arg Met His Gly Leu Asn Ala Ala Leu Asp Asn Leu Arg Lys Val Val
        115                 120                 125

CCT TGC TAT TCT AAG ACG CAG AAG CTG TCC AAA ATC GAG ACT CTG CGC                 488
Pro Cys Tyr Ser Lys Thr Gln Lys Leu Ser Lys Ile Glu Thr Leu Arg
    130                 135                 140

TTG GCC AAG AAC TAC ATC TGG GCT CTG TCG GAG ATC                                 524
Leu Ala Lys Asn Tyr Ile Trp Ala Leu Ser Glu Ile
145                 150                 155
```

( 2 ) INFORMATION FOR SEQ ID NO:9:

( i ) SEQUENCE CHARACTERISTICS:
        ( A ) LENGTH: 156 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Thr Lys Ser Tyr Ser Glu Ser Gly Leu Met Gly Glu Pro Gln Pro
 1           5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
```

```
                    130                      135                      140
Leu Ala Lys Asn Tyr  Ile Trp Ala Leu Ser  Glu Ile
145                      150                      155
```

( 2 ) INFORMATION FOR SEQ ID NO:10:

( i ) SEQUENCE CHARACTERISTICS:
        ( A ) LENGTH: 1352 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: 14B1

( i x ) FEATURE:
        ( A ) NAME/KEY: CDS
        ( B ) LOCATION: 55..1194

( x i ) SEQUENCE DESCRIPTION: SEQ ID NO:10:

```
CCCCTCACTT  TGTGCTGTCT  GTCTCCCCTT  CCCGCCCGGG  GNCCCTCAGG  CACCATGCTG     60

ACCCGCCTGT  TCAGCGAGCC  CGGCCTTCTC  TCGGACGTGC  CCAAGTTCGC  CAGCTGGGGC    120

GACGGCGAAG  ACGACGAGCC  GAGGAGCGAC  AAGGGCGACG  CGCCGCCACC  GCCACCGCCT    180

GCGCCCGGGC  CAGGGGCTCC  GGGGCCAGCC  CGGGCGGCCA  AGCCAGTCCC  TCTCCGTGGA    240

GAAGAGGGGA  CGGAGGCCAC  GTTGGCCGAG  GTCAAGGAGG  AAGGCGAGCT  GGGGGGAGAG    300

GAGGAGGAGG  AAGAGGAGGA  GGAAGAAGGA  CTGGACGAGG  CGGAGGGCGA  GCGGCCCAAG    360

AAGCGCGGGC  CCAAGAAGCG  CAAGATGACC  AAGGCGCGCT  GGAGCGCTC   CAAGCTTCGG    420

CGGCAGAAGG  CGAACGCGCG  GGAGCGCAAC  CGCATGCACG  ACCTGAACGC  AGCCCTGGAC    480

AACCTGCGCA  AGGTGGTGCC  CTGCTACTCC  AAGACGCAGA  AGCTGTCCAA  GATCGAGACG    540

CTGCGCCTAG  CCAAGAACTA  TATCTGGGCG  CTCTCGGAGA  TCCTGCGCTC  CGGCAAGCGG    600

CCAGACCTAG  TGTCCTACGT  GCAGACTCTG  TGCAAGGGTC  TGTCGCAGCC  CACCACCAAT    660

CTGGTGGCCG  GCTGTCTGCA  GCTCAACTCT  CGCAACTTCC  TCACGGAGCA  AGGCCGCGAC    720

GGTGCGNNCC  GCTTCCACGG  CTCGGGCGGC  CCGTTCGCCA  TGCACCCCTA  CCCGTACCCG    780

TGCTCGCGTG  GCGGGCGGAC  AGTGCCAGGC  GCGGCGGCCT  GGGCGGCGGC  CGGCGCACGC    840

CTGCGGACCC  ACGGCTACTG  CGCCGCCTAC  GAGACGCTGT  ATGCGGCGGC  AGGCGGTGGC    900

GGCGCGAGCC  CGGACTACAA  CAGCTCCGAG  TACGAGGGCC  CGCTCAGCCC  CCGCTCTGT    960

CTCAATGGCA  ACTTCTCACT  CAAGCAGGAC  TCCTCGCCCG  ACCACGAGAA  AAGCTACCAC   1020

TACTCTATGC  ACTACTCGGG  CTGCCCNGGT  TCGCGCCACG  GNCACGGGCT  AGTCTTCGGC   1080

TCGTCGGCTG  TGCGCGGGGG  CGTCCACTCG  GAGAATCTCT  TGTCTTACGA  TATGCACCTT   1140

CACCACGANC  GGGGCCCCAT  GTNCNAGGAG  CTCAATGCGT  TTTTCATAA   CTGAGACTTC   1200

GCGCCGNCTC  CCTNCTTTTT  CTTTTGCCTT  TGCCCGCCCC  CCTGTCCCCA  GCCCCAGAG    1260

CGCAGGGACA  CCCCCATNCT  ACCCCGGCNC  CGGCGGAGCG  GGCCACCGGT  CTGCCGCTCT   1320

CCTGGGGCAG  CGCAGTCTGT  TACNTGTGGT  GG                                  1352
```

( 2 ) INFORMATION FOR SEQ ID NO:11:

( i ) SEQUENCE CHARACTERISTICS:
        ( A ) LENGTH: 379 amino acids
        ( B ) TYPE: amino acid ( D ) TOPOLOGY: linear ( i i ) MOLECULE TYPE: protein ( v i ) ORIGINAL SOURCE:
  ( A ) ORGANISM: Homo sapiens ( x i ) SEQUENCE DESCRIPTION: SEQ ID NO:11:

```
Met Leu Thr Arg Leu Phe Ser Glu Pro Gly Leu Leu Ser Asp Val Pro
 1               5                  10                  15

Lys Phe Ala Ser Trp Gly Asp Gly Glu Asp Asp Glu Pro Arg Ser Asp
                20                  25                  30

Lys Gly Asp Ala Pro Pro Pro Pro Pro Ala Pro Gly Pro Gly Ala
                35                  40                  45

Pro Gly Pro Ala Arg Ala Ala Lys Pro Val Pro Leu Arg Gly Glu Glu
 50                  55                          60

Gly Thr Glu Ala Thr Leu Ala Glu Val Lys Glu Glu Gly Glu Leu Gly
 65                  70                  75                  80

Gly Glu Glu Glu Glu Glu Glu Glu Glu Glu Gly Leu Asp Glu Ala
                     85                  90                  95

Glu Gly Glu Arg Pro Lys Lys Arg Gly Pro Lys Lys Arg Lys Met Thr
                100                 105                 110

Lys Ala Arg Leu Glu Arg Ser Lys Leu Arg Arg Gln Lys Ala Asn Ala
                115                 120                 125

Arg Glu Arg Asn Arg Met His Asp Leu Asn Ala Ala Leu Asp Asn Leu
130                 135                 140

Arg Lys Val Val Pro Cys Tyr Ser Lys Thr Gln Lys Leu Ser Lys Ile
145                 150                 155                 160

Glu Thr Leu Arg Leu Ala Lys Asn Tyr Ile Trp Ala Leu Ser Glu Ile
                165                 170                 175

Leu Arg Ser Gly Lys Arg Pro Asp Leu Val Ser Tyr Val Gln Thr Leu
                180                 185                 190

Cys Lys Gly Leu Ser Gln Pro Thr Thr Asn Leu Val Ala Gly Cys Leu
                195                 200                 205

Gln Leu Asn Ser Arg Asn Phe Leu Thr Glu Gln Gly Arg Asp Gly Ala
210                 215                 220

Xaa Arg Phe His Gly Ser Gly Gly Pro Phe Ala Met His Pro Tyr Pro
225                 230                 235                 240

Tyr Pro Cys Ser Arg Gly Gly Arg Thr Val Pro Gly Ala Ala Ala Trp
                245                 250                 255

Ala Ala Ala Gly Ala Arg Leu Arg Thr His Gly Tyr Cys Ala Ala Tyr
                260                 265                 270

Glu Thr Leu Tyr Ala Ala Ala Gly Gly Gly Gly Ala Ser Pro Asp Tyr
                275                 280                 285

Asn Ser Ser Glu Tyr Glu Gly Pro Leu Ser Pro Pro Leu Cys Leu Asn
                290                 295                 300

Gly Asn Phe Ser Leu Lys Gln Asp Ser Ser Pro Asp His Glu Lys Ser
305                 310                 315                 320

Tyr His Tyr Ser Met His Tyr Ser Gly Cys Pro Gly Ser Arg His Gly
                325                 330                 335

His Gly Leu Val Phe Gly Ser Ser Ala Val Arg Gly Gly Val His Ser
                340                 345                 350

Glu Asn Leu Leu Ser Tyr Asp Met His Leu His His Xaa Arg Gly Pro
                355                 360                 365

Met Xaa Xaa Glu Leu Asn Ala Phe Phe His Asn
                370                 375
```

( 2 ) INFORMATION FOR SEQ ID NO:12:

( i ) SEQUENCE CHARACTERISTICS:
        ( A ) LENGTH: 310 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: 20A1

( i x ) FEATURE:
        ( A ) NAME/KEY: CDS
        ( B ) LOCATION: 1..310

( x i ) SEQUENCE DESCRIPTION: SEQ ID NO:12:

```
CCCGGGCGTN CTGAGGTCCA GGGGCACAGG ACGACGAGCA GGAGAGGCGG CGGCGGCCGG      60
ACGCGNGTCC CTCCGAGGCG CTGCTGCACN CGCTGCGCAG GAGCGGCGCG TCAAGGCCAA     120
CGATCGCGAG CGCAACCGCA TGCACAACTT GAACGCGGCC CTGGACGCAC TGCGCAGCGT     180
GCTGCCCTCG TTCCCCGACG ACACCAAGCT CACCAAAATC GAGAGCCTGC GTTNCGCCTA     240
CAACTACATC TGGGCTCTGG CCGAGACACT GCGCTGGCGG ATNAAGGGCT GCCCGGAGGC     300
GGTGCCCGGG                                                           310
```

( 2 ) INFORMATION FOR SEQ ID NO:13:

( i ) SEQUENCE CHARACTERISTICS:
        ( A ) LENGTH: 103 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:13:

```
Pro Gly Val Leu Arg Ser Arg Gly Thr Gly Arg Arg Ala Gly Glu Ala
1               5                   10                  15
Ala Ala Ala Gly Arg Xaa Ser Leu Arg Gly Ala Ala Ala Xaa Ala Ala
            20                  25                  30
Gln Glu Arg Arg Val Lys Ala Asn Asp Arg Glu Arg Asn Arg Met His
        35                  40                  45
Asn Leu Asn Ala Ala Leu Asp Ala Leu Arg Ser Val Leu Pro Ser Phe
    50                  55                  60
Pro Asp Asp Thr Lys Leu Thr Lys Ile Glu Ser Leu Arg Xaa Ala Tyr
65                  70                  75                  80
Asn Tyr Ile Trp Ala Leu Ala Glu Thr Leu Arg Trp Arg Xaa Lys Gly
                85                  90                  95
Cys Pro Glu Ala Val Pro Gly
            100
```

( 2 ) INFORMATION FOR SEQ ID NO:14:

( i ) SEQUENCE CHARACTERISTICS:
        ( A ) LENGTH: 1560 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
  ( A ) ORGANISM: Homo sapiens ( v i i ) IMMEDIATE SOURCE:
  ( B ) CLONE: HC2A ( i x ) FEATURE:
  ( A ) NAME/KEY: CDS
  ( B ) LOCATION: 57..1126

( x i ) SEQUENCE DESCRIPTION: SEQ ID NO:14:

| | | | | | | |
|---|---|---|---|---|---|---|
| TTTTTCTGCT | TTTCTTTCTG | TTTGCCTCTC | CCTTGTTGAA | TGTAGGAAAT | CGAAACATGA | 60 |
| CCAAATCGTA | CAGCGAGAGT | GGGCTGATGG | GCGAGCCTCA | GCCCCAAGGT | CCTCCAAGCT | 120 |
| GGACAGACGA | GTGTCTCAGT | TCTCAGGACG | AGGAGCACGA | GGCAGACAAG | AAGGAGGACG | 180 |
| ACCTCGAAGC | CATGAACGCA | GAGGAGGACT | CACTGAGGAA | CGGGGGAGAG | GAGGAGGACG | 240 |
| AAGATGAGGA | CCTGGAAGAG | GAGGAAGAAG | AGGAAGAGGA | GGATGACGAT | CAAAAGCCCA | 300 |
| AGAGACGCGG | CCCCAAAAAG | AAGAAGATGA | CTAAGGCTCG | CCTGGAGCGT | TTTAAATTGA | 360 |
| GACGCATGAA | GGCTAACGCC | CGGGAGCGGA | ACCGCATGCA | CGGACTGAAC | GCGGCGCTAG | 420 |
| ACAACCTGCG | CAAGGTGGTG | CCTTGCTATT | CTAAGACGCA | GAAGCTGTCC | AAAATCGAGA | 480 |
| CTCTGCGCTT | GGCCAAGAAC | TACATCTGGG | CTCTGTCGGA | GATCCTGCGC | TCAGGCAAAA | 540 |
| GCCCAGACCT | GGTCTCCTTC | GTTCAGACGC | TTTGCAAGGG | CTTATCCCAA | CCCACCACCA | 600 |
| ACCTGGTTGC | GGGCTGCCTG | CAACTCAATC | CTCGGACTTT | TCTGCCTGAG | CAGAACCAGG | 660 |
| ACATGCCCCC | GCACCTGCCG | ACGGCCAGCG | CTTCCTTCCC | TGTACACCCC | TACTCCTACC | 720 |
| AGTCGCCTGG | GCTGCCCAGT | CCGNCTTACG | GTACCATGGA | CAGCTCCCAT | GTCTTCCACG | 780 |
| TTAAGCCTCC | GCCGCACGCC | TACAGCGCAG | CGCTGGAGCC | CTTCTTTGAA | AGCCCTCTGA | 840 |
| CTGATTGCAC | CAGCCCTTCC | TTTGATGGAC | CCCTCAGCCC | GCCGCTCAGC | ATCAATGGCA | 900 |
| ACTTCTCTTT | CAAACACGAA | CCGTCCGCCG | AGTTTGAGAA | AAATTATGCC | TTTACCATGC | 960 |
| ACTATCCTGC | AGCGACACTG | GCAGGGGCCC | AAAGCCACGG | ATCAATCTTC | TCAGGCACCG | 1020 |
| CTGCCCCTCG | CTGCGAGATC | CCCATAGACA | ATATTATGTC | CTTCGATAGC | CATTCACATC | 1080 |
| ATGAGCGAGT | CATGAGTGCC | CAGCTCAATG | CCATATTTCA | TGATTAGAGG | CACGCCAGTT | 1140 |
| TCACCATTTC | CGGGAAACGA | ACCCACTGTG | CTTACAGTGA | CTGTCGTGTT | TACAAAAGGC | 1200 |
| AGCCCTTTGG | TACTACTGCT | GCAAAGTGCA | AATACTCCAA | GCTTCAAGTG | ATATATGTAT | 1260 |
| TTATTGTCAT | TACTGCCTTT | GGAAGAAACA | GGGGATCAAA | GTTCCTGTTC | ACCTTATGTA | 1320 |
| TTATTTTCTA | TAGACTCTTC | TATTTTAAAA | AATAAAAAAA | TACAGTAAAG | TTTAAAAAAT | 1380 |
| ACACCACGAA | TTTGGTGTGG | CTGTATTCAG | ATCGTATTAA | TTATCTGATC | GGGATAACAA | 1440 |
| AATCACAAGC | AATAATTAGG | ATCTATGCAA | TTTTTAAACT | AGTAATGGGC | CAATTAAAAT | 1500 |
| ATATATAAAT | ATATATTTCA | ACCAGCATTT | TACTACTTGT | TACCTCCCAT | GCTGAATTAT | 1560 |

( 2 ) INFORMATION FOR SEQ ID NO:15:

( i ) SEQUENCE CHARACTERISTICS:
    ( A ) LENGTH: 356 amino acids
    ( B ) TYPE: amino acid
    ( D ) TOPOLOGY: linear ( i i ) MOLECULE TYPE: protein ( v i ) ORIGINAL SOURCE:
    ( A ) ORGANISM: Homo sapiens ( x i ) SEQUENCE DESCRIPTION: SEQ ID NO:15:

```
Met Thr Lys Ser Tyr Ser Glu Ser Gly Leu Met Gly Glu Pro Gln Pro
 1               5                  10                  15
Gln Gly Pro Pro Ser Trp Thr Asp Glu Cys Leu Ser Ser Gln Asp Glu
                20                  25                  30
Glu His Glu Ala Asp Lys Lys Glu Asp Asp Leu Glu Ala Met Asn Ala
            35                  40                  45
Glu Glu Asp Ser Leu Arg Asn Gly Gly Glu Glu Glu Asp Glu Asp Glu
        50                  55                  60
Asp Leu Glu Glu Glu Glu Glu Glu Glu Glu Asp Asp Asp Gln Lys
 65                  70                  75                  80
Pro Lys Arg Arg Gly Pro Lys Lys Lys Met Thr Lys Ala Arg Leu
                    85                  90                  95
Glu Arg Phe Lys Leu Arg Arg Met Lys Ala Asn Ala Arg Glu Arg Asn
                100                 105                 110
Arg Met His Gly Leu Asn Ala Ala Leu Asp Asn Leu Arg Lys Val Val
            115                 120                 125
Pro Cys Tyr Ser Lys Thr Gln Lys Leu Ser Lys Ile Glu Thr Leu Arg
        130                 135                 140
Leu Ala Lys Asn Tyr Ile Trp Ala Leu Ser Glu Ile Leu Arg Ser Gly
145                 150                 155                 160
Lys Ser Pro Asp Leu Val Ser Phe Val Gln Thr Leu Cys Lys Gly Leu
                165                 170                 175
Ser Gln Pro Thr Thr Asn Leu Val Ala Gly Cys Leu Gln Leu Asn Pro
                180                 185                 190
Arg Thr Phe Leu Pro Glu Gln Asn Gln Asp Met Pro Pro His Leu Pro
            195                 200                 205
Thr Ala Ser Ala Ser Phe Pro Val His Pro Tyr Ser Tyr Gln Ser Pro
        210                 215                 220
Gly Leu Pro Ser Pro Xaa Tyr Gly Thr Met Asp Ser Ser His Val Phe
225                 230                 235                 240
His Val Lys Pro Pro Pro His Ala Tyr Ser Ala Ala Leu Glu Pro Phe
                245                 250                 255
Phe Glu Ser Pro Leu Thr Asp Cys Thr Ser Pro Ser Phe Asp Gly Pro
                260                 265                 270
Leu Ser Pro Pro Leu Ser Ile Asn Gly Asn Phe Ser Phe Lys His Glu
            275                 280                 285
Pro Ser Ala Glu Phe Glu Lys Asn Tyr Ala Phe Thr Met His Tyr Pro
        290                 295                 300
Ala Ala Thr Leu Ala Gly Ala Gln Ser His Gly Ser Ile Phe Ser Gly
305                 310                 315                 320
Thr Ala Ala Pro Arg Cys Glu Ile Pro Ile Asp Asn Ile Met Ser Phe
                325                 330                 335
Asp Ser His Ser His His Glu Arg Val Met Ser Ala Gln Leu Asn Ala
            340                 345                 350
Ile Phe His Asp
        355
```

( 2 ) INFORMATION FOR SEQ ID NO:16:

( i ) SEQUENCE CHARACTERISTICS:
( A ) LENGTH: 1462 base pairs
( B ) TYPE: nucleic acid
( C ) STRANDEDNESS: single
( D ) TOPOLOGY: linear (i i) MOLECULE TYPE: cDNA (v i) ORIGINAL SOURCE:
  (A) ORGANISM: Mus musculus (v i i) IMMEDIATE SOURCE:
  (B) CLONE: 1.1.1

(i x) FEATURE:
  (A) NAME/KEY: CDS
  (B) LOCATION: 231..1101

(x i) SEQUENCE DESCRIPTION: SEQ ID NO:16:

```
GAATTCAAGC TAGAGGCTGG TACCCCGCCT GGTAGAGATG CCACACTCGC TCCGCGGCTC      60
GCATGGCGCT CTGAAGACGC CGGCGCCCGC CGCCTTGAGG AACCGCTGCC CCCGCTCCCT     120
GAAGATGGGG GAACAATGAA ATAAGCGAGA AGATTCCTCT TCTCCCCCCT CTCTCTCTTG     180
CCCCCTCCCC CCTCCCCTCC CCTCTCCCCT TGACTCCTCT CTGAGGCACC ATGCTGACCC     240
GCCTGTTCAG CGAGCCCGGC CTCCTCTCGG ACGTGCCCAA GTTCGCCAGC TGGGGCGACG     300
GCGACGACGA CGAGCCGAGG AGCGACAAGG GCGACGCGCC GCCGCAGCCT TCTCCTGCTC     360
CCGGGTCGGG GGCTCCAGGA CCCGCCGGGG CCGCCAAGCC AGTGTCTCTT CGTGGAGGAG     420
AAGAGATCCC TGAACCCACG TTGGCTGAGG TCAAGGAGGA AGGAGAGCTG GGCGGCGAGG     480
AGGAGGAGGA AGAGGAGGAG GAGGAAGGAC TGGACGAGGC GGAAGGCGAG CGGCCCAAGA     540
AGCGCGGGCC GAAGAAACGC AAGATGACCA AGGCGCGTCT GGAGCGCTCC AAGCTGCGGC     600
GACAGAAGGC CAATGCGCGC GAGCGCAACC GCATGCACGA CCTGAACGCG GCTCTGGACA     660
ACCTGCGCAA GGTGGTCCCC TGCTACTCCA AGACCCAGAA GCTGTCCAAG ATCGAGACCC     720
TGCGCCTGGC CAAGAACTAC ATCTGGGCTC TCTCGGAGAT CTTGCGCTCC GGGAAGCGGC     780
CGGATCTGGT GTCCTACGTG CAGACTCTGT GCAAGGGGCT GTCACAGCCC ACCACGAATC     840
TGGTGGCCGG CTGCCTGCAG TTAAACTCTC GTAACTTCCT CACGGAGCAG GGCGCGGACG     900
GCGGCCGCTT TCACGGCTCG GGTGGCCCGT TCGCCATGCA TCCGTACCCA TACCCGTGCT     960
CCCGCCTGGC AGGCCACAGT GTCAGGCGGC TGGCGGCCTG GCGGAGGNC GGCGCACGCC    1020
TGCGGACCCA CGGCTACTGC GCCGCCTACG AGACGCTGTA CGCGGCGGCC GGTGGCGGCG    1080
GCGCTAGCCC GGACTACAAC AGCTCCGAGT ACGAGGGTCC ACTCAGTCCC CCGCTCTGTC    1140
TCAACGGCAA CTTCTCGCTC AAGCAGGACT CGTCCCCCGA TCACGAGAAG AGCTACCACT    1200
ACTCTATGCA CTACTCGCGC TGCCCNGGCT CACGCCACGG NCACGGGCTG GTCTTCGGCT    1260
CGTCGGCCGT GCGCGGGGGC GTCCACTCCG AGAATCTCTT GTCTTACGAT ATGCACCTTC    1320
ACCACGATCG GGGCCCCATG TACGAGGAGC TCAACGCATT TTTCCATAAC TGAGACCTCN    1380
CGCCGACCCC TTCTTTTTCT TTGCCTTNNT CCGGCCCCTT AGCCCCANCC CCAANANCTC    1440
AGGNNTCCCA CCGATCTCCA GG                                            1462
```

(2) INFORMATION FOR SEQ ID NO:17:

(i) SEQUENCE CHARACTERISTICS:
    (A) LENGTH: 380 amino acids
    (B) TYPE: amino acid
    (D) TOPOLOGY: linear (i i) MOLECULE TYPE: protein (v i) ORIGINAL SOURCE:
    (A) ORGANISM: Mus musculus (x i) SEQUENCE DESCRIPTION: SEQ ID NO:17:

```
Met Leu Thr Arg Leu Phe Ser Glu Pro Gly Leu Leu Ser Asp Val Pro
```

| | 1 | | | 5 | | | | | 10 | | | | | 15 | |
|---|---|---|---|---|---|---|---|---|---|---|---|---|---|---|---|

Lys Phe Ala Ser Trp Gly Asp Gly Asp Asp Glu Pro Arg Ser Asp
           20                    25                30

Lys Gly Asp Ala Pro Pro Gln Pro Ser Pro Ala Pro Gly Ser Gly Ala
            35                    40                    45

Pro Gly Pro Ala Arg Ala Ala Lys Pro Val Ser Leu Arg Gly Gly Glu
        50                    55                    60

Glu Ile Pro Glu Pro Thr Leu Ala Glu Val Lys Glu Glu Gly Glu Leu
65                    70                    75                    80

Gly Gly Glu Glu Glu Glu Glu Glu Glu Glu Glu Gly Leu Asp Glu
                    85                    90                    95

Ala Glu Gly Glu Arg Pro Lys Lys Gly Pro Lys Lys Arg Lys Met
                100                    105                110

Thr Lys Ala Arg Leu Glu Arg Ser Lys Leu Arg Arg Gln Lys Ala Asn
            115                    120                    125

Ala Arg Glu Arg Asn Arg Met His Asp Leu Asn Ala Ala Leu Asp Asn
        130                    135                    140

Leu Arg Lys Val Val Pro Cys Tyr Ser Lys Thr Gln Lys Leu Ser Lys
145                    150                    155                    160

Ile Glu Thr Leu Arg Leu Ala Lys Asn Tyr Ile Trp Ala Leu Ser Glu
                165                    170                    175

Ile Leu Arg Ser Gly Lys Arg Pro Asp Leu Val Ser Tyr Val Gln Thr
            180                    185                    190

Leu Cys Lys Gly Leu Ser Gln Pro Thr Thr Asn Leu Val Ala Gly Cys
        195                    200                    205

Leu Gln Leu Asn Ser Arg Asn Phe Leu Thr Glu Gln Gly Ala Asp Gly
210                    215                    220

Gly Arg Phe His Gly Ser Gly Gly Pro Phe Ala Met His Pro Tyr Pro
225                    230                    235                    240

Tyr Pro Cys Ser Arg Leu Ala Gly His Ser Val Arg Arg Leu Ala Ala
                245                    250                    255

Trp Ala Glu Xaa Gly Ala Arg Leu Arg Thr His Gly Tyr Cys Ala Ala
            260                    265                    270

Tyr Glu Thr Leu Tyr Ala Ala Ala Gly Gly Gly Gly Ala Ser Pro Asp
        275                    280                    285

Tyr Asn Ser Ser Glu Tyr Glu Gly Pro Leu Ser Pro Pro Leu Cys Leu
290                    295                    300

Asn Gly Asn Phe Ser Leu Lys Gln Asp Ser Ser Pro Asp His Glu Lys
305                    310                    315                    320

Ser Tyr His Tyr Ser Met His Tyr Ser Arg Cys Pro Gly Ser Arg His
                325                    330                    335

Gly His Gly Leu Val Phe Gly Ser Ser Ala Val Arg Gly Val His
            340                    345                    350

Ser Glu Asn Leu Leu Ser Tyr Asp Met His Leu His His Asp Arg Gly
        355                    360                    365

Pro Met Tyr Glu Glu Leu Asn Ala Phe Phe His Asn
370                    375                    380

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear

```
        ( i i ) MOLECULE TYPE: cDNA ( v i i ) IMMEDIATE SOURCE:
                    ( B ) CLONE: JL34

( x i ) SEQUENCE DESCRIPTION: SEQ ID NO:18:

CTCAGCATCA GCAACTCGGC                                                           20

( 2 ) INFORMATION FOR SEQ ID NO:19:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: cDNA ( v i i ) IMMEDIATE SOURCE:
                    ( B ) CLONE: JL36

( x i ) SEQUENCE DESCRIPTION: SEQ ID NO:19:

TCGGATCCCG TTCTAGGCGC GCCTTGGTC                                                 29

( 2 ) INFORMATION FOR SEQ ID NO:20:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: cDNA ( v i i ) IMMEDIATE SOURCE:
                    ( B ) CLONE: JL40

( x i ) SEQUENCE DESCRIPTION: SEQ ID NO:20:

GTTTTCCCAG TCACGACGTT G                                                         21
```